(12) United States Patent
Staten et al.

(10) Patent No.: US 11,029,318 B2
(45) Date of Patent: Jun. 8, 2021

(54) METHODS FOR PREDICTING AND TREATING PATIENTS WITH INCREASED RISK OF ADVERSE PREGNANCY OUTCOME

(71) Applicant: Kypha, Inc., St. Louis, MO (US)

(72) Inventors: Nicholas Staten, Kirkwood, MO (US); Alfred Kim, St. Louis, MO (US); Paul Olson, St. Louis, MO (US)

(73) Assignee: Kypha, Inc., St. Louis, MO (US)

( * ) Notice: Subject to any disclaimer, the term of this patent is extended or adjusted under 35 U.S.C. 154(b) by 14 days.

(21) Appl. No.: 15/756,294

(22) PCT Filed: Aug. 26, 2016

(86) PCT No.: PCT/US2016/048874
§ 371 (c)(1),
(2) Date: Feb. 28, 2018

(87) PCT Pub. No.: WO2017/040243
PCT Pub. Date: Mar. 9, 2017

(65) Prior Publication Data
US 2018/0275139 A1    Sep. 27, 2018

Related U.S. Application Data

(60) Provisional application No. 62/236,004, filed on Oct. 1, 2015, provisional application No. 62/211,548, filed on Aug. 28, 2015.

(51) Int. Cl.
*G01N 33/53* (2006.01)
*G01N 33/68* (2006.01)
*A61K 45/06* (2006.01)
*A61K 31/573* (2006.01)

(52) U.S. Cl.
CPC ....... *G01N 33/6893* (2013.01); *A61K 31/573* (2013.01); *A61K 45/06* (2013.01); *G01N 33/68* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,474,927 A * | 12/1995 | Anderson | G01N 33/689 435/7.21 |
| 8,865,164 B2 | 10/2014 | Olson et al. | |
| 2005/0271658 A1 | 12/2005 | Brunetta et al. | |
| 2007/0292421 A1 * | 12/2007 | Feinberg | A61K 31/395 424/135.1 |
| 2008/0188829 A1 * | 8/2008 | Creasy | A61P 15/06 604/522 |
| 2009/0110667 A1 | 4/2009 | Mozaffarian et al. | |
| 2012/0135430 A1 * | 5/2012 | Zhang | G01N 33/566 435/7.92 |
| 2012/0141457 A1 * | 6/2012 | Olson | A61P 13/12 424/130.1 |
| 2013/0283404 A1 | 10/2013 | Richardson et al. | |
| 2014/0057295 A1 | 2/2014 | Stegmann et al. | |
| 2014/0186332 A1 * | 7/2014 | Ezrin | G01N 33/689 424/130.1 |

FOREIGN PATENT DOCUMENTS

WO    WO-2017/040243 A1    3/2017

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Petri et al., Treatment of Systemic Lupus Erythematosus: An Update, Am Fam Physician, Jun 1, 1998;57 (11), pp. 1-6. (Year: 1998).*
Catania, R. A. and Chaudry, I. H., Immunological consequences of trauma and shock, Ann. Acad. Med. Singapore, 28:120-32 (1999).
Hecke, F. et al., Circulating complement proteins in multiple trauma patients-correlation with injury seventy, development of sepsis, and outcome, Gilt. Care Med., 25(12): 201524 (1997).
Huber-Lang, M. S. et al., Complement-induced impairment of innate immunity during sepsis, J. Immunol., 169:3223-31 (2002).
International Search Report for PCT/US2016/048874, 3 pages (dated Oct. 24, 2016).
Kang, H. J. et al., Change of complement system predicts the outcome of patients with severe thermal injury, J. Burn Care Rehabil., 24: 148-53 (2003).
Written Opinion for PCT/US2016/048874, 10 pages (dated Oct. 24, 2016).
Younger, J. G. et al., Detrimental effects of complement activation in hemorrhagic shock, J. Appl. Physiol. 90:441-46 (2001).

* cited by examiner

*Primary Examiner* — Gary Counts
(74) *Attorney, Agent, or Firm* — Choate, Hall & Stewart LLP; Brian E. Reese; Maria C. Smith

(57) ABSTRACT

In some embodiments, the present invention provides methods for treating pregnant patients at risk of adverse pregnancy outcome, including, in some embodiments, by measuring one or more of a level of iC3b, intact C3, and total C3.

12 Claims, 5 Drawing Sheets

METHODS FOR PREDICTING AND TREATING PATIENTS WITH INCREASED RISK OF ADVERSE PREGNANCY OUTCOME

CROSS-REFERENCE TO RELATED APPLICATIONS

This application claims the benefit of U.S. Application Ser. No. 62/211,548 filed on Aug. 28, 2015 and U.S. Application Ser. No. 62/236,004 filed on Oct. 1, 2015, the disclosures of which are hereby incorporated by reference in their entireties.

BACKGROUND

Autoimmune disease develops when the body's immune system decides healthy cells are foreign and attacks healthy cells. There are various types of autoimmune diseases, for instance, lupus erythematosus, preeclampsia, and vasculitis. For example, lupus erythematosus is a collection of autoimmune diseases in which the human immune system becomes dysfunctional and attacks the body's own healthy tissue. The course of these diseases are highly variable and almost any tissue in the body can be affected. One commonality among these diseases is that they are characterized in that sufferers often experience periods of disease progression, also called flares, alternating with periods of relative disease inactivity, called remissions. There is presently no cure for any form of autoimmune disease, and no satisfactory diagnostic to aid in diagnosing, monitoring, or treating the disease.

SUMMARY

The present invention is based, in part, on the surprising discovery that certain complement proteins and/or split products, ratios between complement split products and/or proteins, and/or changes in the level(s) of complement proteins and/or split products (percent or magnitude, for example) may be useful in the prediction of flares in various forms of autoimmune disease (e.g., lupus erythematosus, the prediction of adverse pregnancy outcomes, including in pregnant women suffering from a lupus erythematosus, vasculitis). Prior to the present invention, several laboratory tests are used to estimate for the presence of flares in patients with autoimmune disease (e.g., lupus erythematosus). However, due to the lack of specificity of these tests for autoimmune disease activity, patients with autoimmune disease may have erroneously been given treatments for non-autoimmune disease symptoms, and some may have been undertreated for an authentic autoimmune disease flare. This has led to improper treatment (both over- and under-treatment) of autoimmune disease patients, and logistical issues with clinical trials studying novel therapies for autoimmune diseases such as lupus. The present invention provides, among other things, methods for predicting flares in autoimmune disease sufferers. In some embodiments, the present invention provides methods for preventing or reducing the severity of a flare. In some embodiments, the present invention provides methods of determining the effectiveness of an autoimmune (e.g., lupus) therapy, including, for example, evaluation of an investigational drug in lupus or other autoimmune disease clinical trials. In some embodiments, provided methods allow for the diagnosis of autoimmune diseases (such as lupus, preeclampsia, or vasculitis) in a subject. The methods provided herein allow for new paradigms in the treatment of autoimmune diseases and an increase in the quality of life for autoimmune disease sufferers.

In some embodiments, the present invention provides methods for predicting flare in subjects with one or more autoimmune diseases, for example, a lupus erythematosus. In some embodiments, pending flares may be reduced in severity and/or prevented from clinical manifestation in their entirety using provided methods. In some embodiments, the present invention provides methods for preventing or reducing the severity of a flare including the steps of determining in a sample from a subject suffering from lupus erythematosus a complement activation potential, administering a treatment or implementing a change in treatment if the complement activation potential is about 25% or higher, wherein a complement activation potential of about 25% or higher indicates that the subject will experience a flare within 30 days. In some embodiments, a complement activation potential of about 25% or higher indicates that the subject will experience a flare within 7 days. In some embodiments, a complement activation potential of about 25% or higher indicates that the subject will experience a flare within 1 day. In some embodiments, administering or implementing a change in treatment results in a decrease in complement activation potential in the subject. In some embodiments, the subject does not experience a flare within 30 days of the administering or implementing a change in treatment.

In some embodiments, the present invention provides methods of determining the effectiveness of a therapy for treating an autoimmune disease, such as lupus erythematosus, including the steps of determining in a sample from a subject suspected of having lupus erythematosus a first complement activation potential, administering at least one treatment to a subject suffering from lupus erythematosus, determining in a sample from a subject suspected of having lupus erythematosus a second complement activation potential, and implementing a change in treatment if the second complement activation potential is equal to or higher than the first complement activation potential. In some embodiments, the second complement activation potential is determined within 3 months of the first complement activation potential. In some embodiments, the second complement activation potential is determined within 1 month of the first complement activation potential.

According to various embodiments, treatment may result in a decrease in the complement activation potential in a subject. In some embodiments, the decrease in complement activation potential occurs within one month from the administration or implementation step. In some embodiments, the decrease in complement activation potential occurs within one week from the administration or implementation step.

In some embodiments, the present invention provides methods for preventing or reducing the severity of an adverse pregnancy outcome including the steps of determining in a sample from a pregnant subject a complement activation potential, and administering a treatment or implementing a change in treatment if the complement activation potential is about 25% or higher (e.g., relative to a previously attained complement activation potential or composite benchmark), wherein a complement activation potential of about 25% or higher indicates that the subject is likely to experience an adverse pregnancy outcome within 3 months.

According to any of a variety of embodiments, the complement activation potential in a sample (and thus in the subject from which it originated) may be assessed through one or more of several measures. In some embodiments, the complement activation potential is determined through one or more of a) detecting a level of iC3b in the sample from the subject, b) determining the ratio between the levels of iC3b and total C3 in the sample from the subject, c) detecting a level of total C3 in the sample from the subject, and d) detecting the level of C4 in the sample from the subject. In some embodiments, at least two of a-d are used to determine the complement activation level in the sample. In some embodiments, provided methods include the use of one or more additional or alternative biomarkers in addition to iC3b, total C3, C4, C4d erythrocyte sedimentation rate (ESR), c-reactive protein (CRP), and double stranded DNA antibodies (dsDNA Ab). It is specifically contemplated that many provided methods will be used to capture changes in complement activation over time in an individual (i.e., longitudinal data). In some embodiments, provided methods may be used to capture complement activation potentials in 1, 2, 5, 10 or more samples over time in order to understand the patient's inflammatory state over time.

According to various embodiments, any of a variety of assays and detecting agents may be used to determine a complement activation potential. In some embodiments, one or more detecting agents are used to determine a complement activation potential in a sample. In some embodiments, the detecting agent may be one or more antibodies. In addition to a variety of detecting agents, various embodiments may make use of any of a variety of assay formats. By way of non-limiting example, in some embodiments, a lateral flow assay is used to determine the complement activation potential in the sample.

In some embodiments, the level or ratio used to determine a complement activation potential in a particular subject may be compared against a reference level or ratio. In some embodiments, the level or ratio is compared against a reference level or ratio, which was obtained from the subject previously. In some embodiments, the level or ratio is compared against a reference level or ratio, which was obtained from a different subject. In some embodiments, the level or ratio is an average level or ratio from two or more samples analyzed over time (e.g., an average level or ratio generated from several measurements or multiple samples from the same patient over a period of time).

According to various embodiments, one or more treatments may be administered and/or the dose or other parameter of an ongoing treatment adjusted in response to a complement activation potential in a subject. By way of non-limiting example, in some embodiments, the at least one treatment is selected from the group consisting of steroids, non-steroidal anti-inflammatory drugs (NSAIDs), hydroxychloroquine, chloroquine, quinacrine, methotrexate, azathioprine, sulfasalazine, cyclophosphamide, chlorambucil, cyclosporine, mycophenolate mofetil, mycophenolate sodium, rituximab, belimumab, complement inhibitors, FK506, cyclosporine, rapamycin, intravenous immunoglobulin, Acthar, plasmapheresis, physical therapy, sleep therapy, and cognitive behavioral therapy. In some embodiments, the at least one treatment is or comprises part of a combination therapy administered to the subject.

In some embodiments, a sample is or comprises one or more body fluids. In some embodiments, the sample is selected from the group consisting of whole blood, serum, plasma, urine, tears, saliva, wound exudate, pus, nasal discharge, feces, bronchoalveolar lavage fluid, and cerebrospinal fluid.

In some embodiments, provided methods allow for rapid determination of a complement activation potential which avoid problems common in many previous tests related to complement activation. For example, many previous tests for complement activation suffered from false positive results as a result of auto-activation of the complement cascade in a sample during the assay or in preparation of the sample for assay. Thus, one of the advantages of some embodiments is that the step of determining is performed under controlled conditions such that performance of the step does not substantially activate complement within the sample. In addition, some embodiments are able to provide very rapid returns of complement activation potential, such that they are amenable to point of care use. For example, in some embodiments, the complement activation level is determined within 30 minutes (e.g., within 20 minutes) of the initiation of the determining step.

Provided methods may be used with subjects suffering from any of a variety of autoimmune diseases, for example, various forms of lupus erythematosus. In some embodiments, the lupus erythematosus is selected from the group consisting of acute cutaneous lupus erythematosus, subacute cutaneous lupus erythematosus, chronic cutaneous lupus erythematosus, discoid lupus erythematosus, chilblain lupus erythematosus, lupus erythematosus-lichen planus overlap syndrome, lupus erythematosus panniculitis, tumid lupus erythematosus, verrucous lupus erythematosus, complement deficiency, syndromes, drug-induced lupus erythematosus, neonatal lupus erythematosus, neuropsychiatric lupus, lupus nephritis, and systemic lupus erythematosus.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
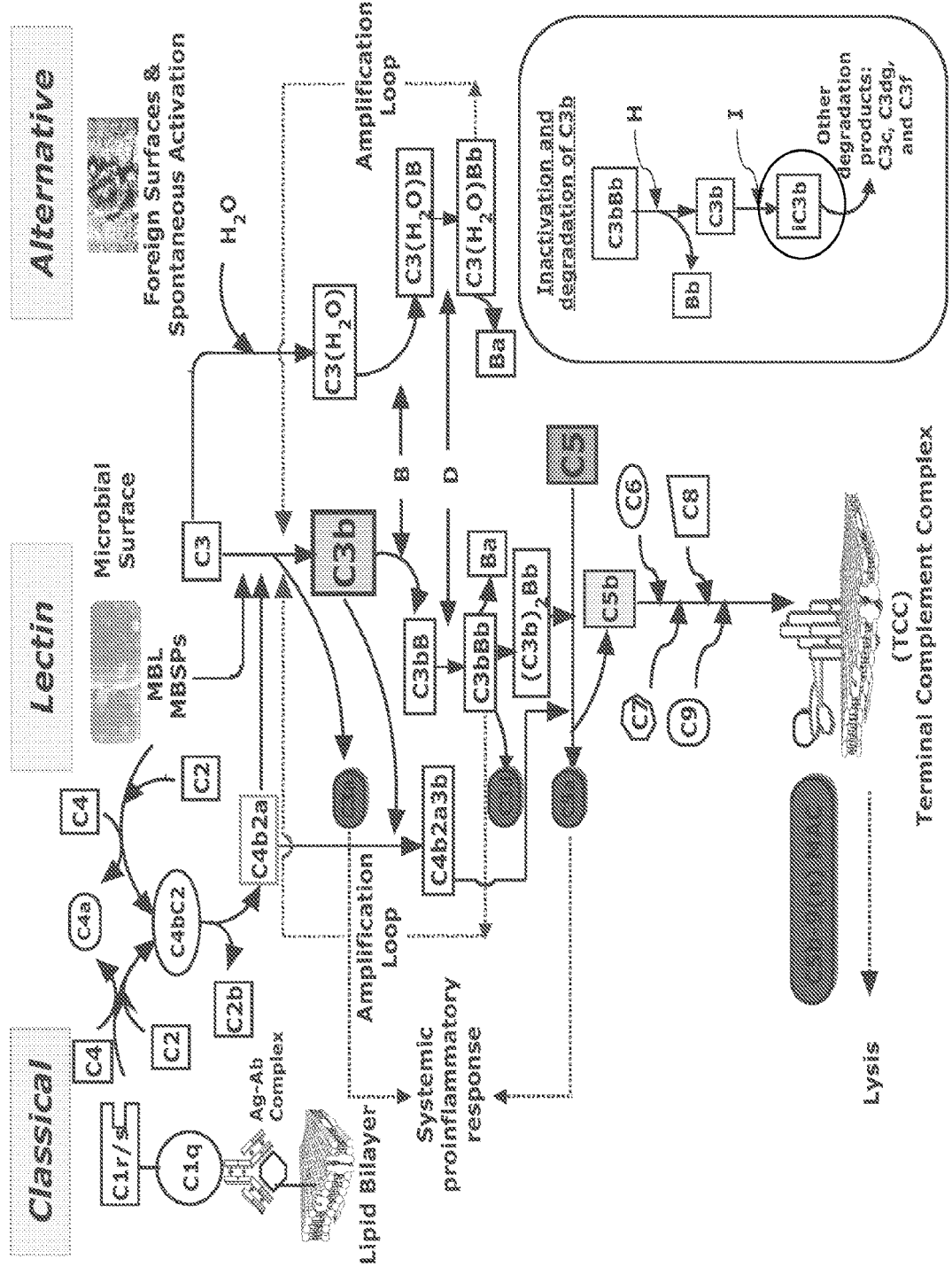
FIG. 1 provides a schematic overview of the complement system. Complement is activated by three major pathways, all of which converge on the activation of intact C3. Proteolytic activation of C3 produces the C3 split products C3a and C3b. C3b is further proteolytically modified to form iC3b, a biomarker for C3 activation. Intact C3 and iC3b are circled in the schematic.

Administration: as used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time.

Agent: the term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, complement receptors or binding proteins, enzymes, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Antibody fragment: as used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

Approximately: as used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biomarker: the term "biomarker" is used herein, consistent with its use in the art, to refer to an entity whose presence, level, or form, correlates with a particular biological event or state of interest, so that it is considered to be a "marker" of that event or state. To give but a few examples, in some embodiments, a biomarker may be or comprises a marker for a particular disease state, or for likelihood that a particular disease, disorder or condition may develop (e.g., a lupus erythematosus). In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), a metabolite, or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, breath condensate, etc.

Combination therapy: as used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Comparable: as used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Detecting agent: the term "detecting agent" as used herein refers to any element, molecule, functional group, compound, fragment or moiety that is detectable. In some embodiments, a detecting agent is provided or utilized alone. In some embodiments, a detecting agent is provided and/or utilized in association with (e.g., joined to) another agent. Examples of detecting agents include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold and/or silver, and the like), biotin, dioxigenin, haptens, and proteins for which antisera or monoclonal antibodies are available. In some embodiments, a detecting agent comprises an antibody. In some embodiments, a detecting agent is or comprises an antibody associated with one of more of the exemplary detecting agents in this paragraph.

Determine: many provided methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosing regimen: (or "therapeutic regimen"), as used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Flare: as used herein, the term "flare" indicates an acute increase in disease severity sufficient to cause a clinician to initiate or alter treatment in a subject. In some embodiments, a flare may be defined as achieving a certain score on one or more disease indices, for example the SELENA SLEDAI Flare Index or the Physician Global Assessment (PGA). In some embodiments, an episodic change of disease activity indicates a flare. In some embodiments, a flare may be characterized or defined by new or increased use of treatments such as high dose prednisone (e.g., greater than 20 mg/day) or immunosuppressives. In some embodiments, a flare may be characterized or defined by hospitalization due to SLE or death due to SLE. In some embodiments, a flare may be or comprise a measurable increase in disease activity in one or more organ systems involving new or worse clinical signs and symptoms and/or laboratory measurements, for example, as compared to a previously taken measurement. In some embodiments, a measurable increase in disease activity is considered clinically significant by the assessor and typically includes at least consideration of a change or an increase in treatment and, quite often, implementing a change in treatment. In some embodiments, flare is characterized by or defined as a change of greater than or equal to 1.0 in the physician's global assessment of disease activity (measured on a 0-3) scale from the previous visit or from a visit within the last 200 days (e.g., last 100 days, e.g., last 93 days, e.g., last 75 days, e.g., last 50 days, e.g., last 25 days, e.g., last 10 days, e.g., last 5 days, e.g., last 1 day).

Improve," "increase" or "reduce": as used herein, or grammatical equivalents thereof, indicate values that are relative to a baseline measurement, such as a measurement in the same individual prior to initiation of a treatment described herein, or a measurement in a control individual (or multiple control individuals) in the absence of the treatment described herein. In some embodiments, a "control individual" is an individual afflicted with the same form of disease or injury as an individual being treated.

In vitro: the term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Prevention or "prevention": as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Reference: as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: as used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. The exact response criteria can be selected in any appropriate manner, provided that the groups to be compared are assessed based on the same or comparable criteria for determining response rate. One of ordinary skill in the art will be able to select appropriate criteria.

Risk: as will be understood from context, "risk" of a disease, disorder, and/or condition comprises likelihood that a particular individual will develop a disease, disorder, and/or condition (e.g., a lupus erythematosus). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., a lupus erythematosus). In some embodiments a reference sample or group of reference samples are from individuals comparable to a particular individual. In some embodiments, relative risk is 0, 1, 2, 3, 4, 5, 6, 7, 8, 9, 10, or more.

Sample: as used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood (e.g., whole blood); blood cells; ascites; tissue or fine needle biopsy samples; cell-containing body fluids; free floating nucleic acids; serum; plasma; sputum; saliva; tears; urine; cerebrospinal fluid; peritoneal fluid; pleural fluid; feces; lymph; gynecological fluids; wound exudate; pus; skin swabs; vaginal swabs; oral swabs; nasal swabs; washings or lavages such as a ductal lavages or broncheoalveolar lavages; aspirates; scrapings; bone marrow specimens; synovial fluid; tissue biopsy specimens; surgical specimens; feces, other body fluids, secretions, and/or excretions such as sweat and ear wax; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Subject: as used herein, the term "subject" or "patient" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: as used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: as used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: a "therapeutic regimen", as that term is used herein, refers to a dosing regimen whose administration across a relevant population may be correlated with a desired or beneficial therapeutic outcome.

Treatment: as used herein, the term "treatment" (also "treat" or "treating") refers to any administration of a substance (e.g., a corticosteroid) that partially or completely alleviates, ameliorates, relives, inhibits, delays onset of, reduces severity of, and/or reduces incidence of one or more symptoms, features, and/or causes of a particular disease, disorder, and/or condition (e.g., lupus erythematosus). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

The present invention provides, inter alia, a variety of new methods and treatment regimen for improving the lives of autoimmune disease sufferers. In some embodiments, the present invention provides methods and treatment regimen for patients with a form of lupus erythematosus. In some embodiments, the present invention provides methods and treatment regimen for patients with preeclampsia. In some embodiments, the present invention provides methods and treatment regimen for patients with vasculitis. In some embodiments, patients may be suffering from two or more diseases, disorders, or conditions.

In some embodiments, the present invention provides methods for predicting flare in subjects with an autoimmune disease, such as lupus erythematosus. In some embodiments, pending flares may be reduced in severity and/or prevented from clinical manifestation in their entirety using provided methods. In some embodiments, the present invention provides methods for diagnosing an autoimmune disease, for example, lupus erythematosus. In some embodiments, the present invention provides methods for preventing or reducing the severity of a flare including the steps of determining in a sample from a subject suffering from an autoimmune disease a complement activation potential, administering a treatment or implementing a change in treatment if the complement activation potential is about 25% or higher, wherein a complement activation potential of about 25% or higher indicates that the subject will experience a flare within 30 days. In some embodiments, a change in complement activation potential is measured from a prior complement activation potential taken from the subject. In some embodiments, a change in complement activation potential is measured from a composite complement activation potential calculated from multiple subjects.

In some embodiments, the present invention provides methods of determining the effectiveness of a therapy for treating an autoimmune disease, for example, lupus erythematosus, including the steps of determining in a sample from a subject suspected of having an autoimmune disease a first complement activation potential, administering at least one treatment to a subject suffering from an autoimmune disease, determining in a sample from a subject suspected of having an autoimmune disease a second complement activation potential, and implementing a change in treatment if the second complement activation potential is equal to or higher than the first complement activation potential.

In some embodiments, provided methods may be used to predict the likelihood of adverse pregnancy outcome (APO), for example, in lupus sufferers. In some embodiments, an APO is pre-term death of a fetus. In some embodiments, an APO is a pre-term livebirth of a fetus. In some embodiments, an APO may be one or more of central nervous system defect, peripheral nervous system defect, the presence of one or more forms of toxicity in the fetus, low birth weight of less than 1,501 grams, neonatal hemorrhage, and a non-nervous system birth defect.

In some embodiments, provided methods may be used to predict an increase in the severity of vasculitis, an autoimmune disease that attacks blood vessels. In some embodiments, vasculitis causes vessel walls to thicken and/or narrow, cutting off vital blood supply to tissues and organs. In some embodiments, symptoms of vasculitis include fever, fatigue, weight loss, and muscle and joint pain. In some embodiments, forms of vasculitis improve on their own. In some embodiments, forms of vasculitis require treatment.

Lupus Erythematosus

Lupus erythematosus (hereinafter "lupus") is a collection of autoimmune diseases in which the human immune system becomes dysfunctional and attacks the body's own healthy tissue. While a normal person's immune system creates antibodies to fight of foreign pathogens such as viruses and/or bacteria, in lupus sufferers, the body creates antibodies against the subject's own proteins, often anti-nuclear antibodies that bind to double stranded DNA.

The course of these diseases are highly variable and almost any tissue in the body can be affected. Some forms of lupus are systemic, while others only affect cutaneous tissue. One commonality among these diseases is that they are characterized in that sufferers often experience periods of disease progression, also called flares, alternating with periods of relative disease inactivity, called remissions. There are several subtypes of lupus, including acute cutaneous lupus erythematosus, subacute cutaneous lupus erythematosus, chronic cutaneous lupus erythematosus, discoid lupus erythematosus, chilblain lupus erythematosus, lupus erythematosus-lichen planus overlap syndrome, lupus erythematosus panniculitis, tumid lupus erythematosus, verrucous lupus erythematosus, complement deficiency, syndromes, drug-induced lupus erythematosus, neonatal lupus erythematosus, neuropsychiatric lupus, lupus nephritis, and systemic lupus erythematosus. The most common form, systemic lupus erythematosus, is briefly described below.

While it is generally known that women suffering from lupus are at an increased risk of maternal and fetal complications from pregnancy, provided methods allow for the prediction of adverse pregnancy outcomes in women suffering from preeclampsia. To our knowledge, this is the first time adverse pregnancy outcomes can be predicted, and thus allow for prophylactic and/or therapeutic treatments. In some embodiments, women suffering from preeclampsia are also suffering from a form of lupus and/or antiphospholipid antibody syndrome (APS). In some embodiments, elevated iC3b levels, an elevated iC3b/total C3 ratio, an elevated iC3b/intact C3 ratio, or a decreased level of total C3 indicates an increased risk for adverse pregnancy outcome. In some embodiments, provided methods include the treatment of the mother and/or fetus in order to reduce the severity of, or even prevent an adverse pregnancy outcome.

Systemic Lupus Erythematosus

Systemic Lupus Erythematosus (SLE), is the most common form of lupus. SLE has a variable course of progression, but can affect any tissue in the body including the heart, joints, lungs, blood vessels, liver, kidneys, and central and peripheral nervous systems. The cause of SLE is presently unknown, though it is suspected to be related to an environmental trigger of some kind which affects genetically susceptible individuals.

Prevalence of SLE varies globally, with estimates ranging from 20 to 70 per 100,000 people. The disease is also nine times more likely to affect women as it is men and strikes most often in women between 15 and 35 years of age. The disease is most common in subjects of African-American, Hispanic, or Asian descent.

Without wishing to be held to a particular theory, SLE is thought to be associated with defects in apoptotic clearance and the pathogenic effect of apoptotic debris remaining in various tissues. Early apoptotic cells express cell-surface protein which act as "eat-me" signals that prompt immune cells to engulf them. Apoptotic cells also express "find-me" signals, to attract macrophages and dendritic cells. When apoptotic material is not removed correctly by phagocytes, they are typically captured instead by antigen-presenting cells, which may lead to development of antinuclear antibodies, among other issues.

Common signs and symptoms of SLE include fever, joint pain, muscle pain, fatigue, and general malaise, among others. Because these signs and symptoms are common and may be associated with other diseases, disorders, or conditions, diagnosis of SLE is often difficult at best. In addition to the above signs and symptoms, certain other symptoms manifest differently between women and men. Specifically, female SLE sufferers often experience greater relapses (i.e. flares), low white blood cell count, a greater degree of arthritis, Raynaud's phenomenon (i.e. greatly reduced blood flow leading to discoloration of the fingers, toes, and possibly other areas), and psychiatric issues. Male SLE sufferers, on the other hand, tend to experience seizure, kidney disease, serositis (i.e. inflammation of lung and/or heart tissue), skin problems, and peripheral neuropathy.

Prior to the present invention, diagnosis of SLE has been difficult at best. In fact, the American College of Rheumatology (ACR) criteria is the most common method currently used by clinicians to diagnose SLE. The issue is that these criteria were designed to provide an operational definition of SLE for the purposes of classification in randomized controlled trials, and not for general clinical diagnosis. As a result, many SLE sufferers do not meet the ACR criteria and are thus at risk for a misdiagnosis. Briefly, a subject is considered to have SLE according to the ACR if he or she has 4 out of 11 of the following symptoms simultaneously or serially on two separate occasions: serositis, oral ulcers, arthritis, photosensitivity (exposure to ultraviolet light causing rash or other flare symptoms), pulmonary fibrosis, hematologic disorder (e.g., hemolytic anemia), renal disorder, Raynaud's, ANA, immunologic (e.g., anti-dsDNA), neuropsychiatric (e.g., seizures or psychosis), malar rash (a rash on the cheeks), and discoid rash (red, scaly patches on the skin that cause scarring).

Generally, treatment of SLE has been limited to immunosuppression and addressing symptoms of flare. Commonly used treatments include, for example, corticosteroids, anti-malarial drugs, anti-metabolite drugs (e.g. mycophenolate mofetil/sodium, azathioprine, methotrexate), alkylating drugs (e.g., cyclophosphamide), hydroxychloroquine (HCQ), non-steroidal anti-inflammatory drugs (NSAIDs), and belimumab. Other treatments used may include other steroids, chloroquine, quinacrine, methotrexate, azathioprine, cyclophosphamide, chlorambucil, cyclosporine, mycophenolate mofetil, rituximab, complement inhibitors, and plasmapheresis.

Preeclampsia

Preeclampsia is a disorder that occurs during pregnancy and the postpartum period and affects both mother and unborn child. Preeclampsia impacts 5-15% of all births worldwide and is responsible for 20% of the 13 million preterm births each year. In the U.S. alone, 100,000 of the total annual 500,000 premature births are a result of preeclampsia annually.

Preeclampsia is characterized by the presence of autoantibodies that activate the major angiotensin receptor, AT1. Studies during the past decade has shown that these autoantibodies activate AT1 receptors on a variety of cell types and provoke biological responses that are relevant to the pathophysiology of preeclampsia, thereby suggesting that preeclampsia is an autoimmune disease.

Preeclampsia involves pregnancy-induced hypertension in which protein is often observed in expectant mothers urine. At present, preeclampsia is diagnosed by an elevation of the expectant mother's blood pressure, usually only after the $20^{th}$ week of pregnancy, combined with the appearance of excessive protein in her urine. Preeclampsia is currently defined by an elevation in blood pressure (about greater than 140/90 mm Hg) and protein in the urine (about greater than 300 mg/24 hours) occurring in the second half of pregnancy in women without a history of high blood pressure, kidney disease, diabetes, or other significant disease. Preeclampsia may also include a myriad of other abnormalities.

No precise way currently exists to diagnose preeclampsia. Thus, the possibility of preeclampsia is typically considered for women displaying those particular symptoms beyond 20 weeks gestation. Preeclampsia has proven particularly difficult to diagnose because its symptoms mimic many other diseases and includes symptoms such as headaches, abdominal pain, visual disturbances, confusion, anxiety, shortness of breath, nausea, and vomiting. If left undiagnosed, or diagnosed too late, there can be a serious impact on both women and their babies. Moreover, preeclampsia can progress from mild to severe rapidly. Serious signs of the disease include high blood pressure, risk of brain injury, impaired kidney and liver function, blood clotting problems, pulmonary edema, and even seizures. Further adding to the complexity of diagnosis, some women exhibit preexisting hypertension, which can make it more difficult to discern from the onset of preeclampsia. Currently, no effective way to diagnose this potentially fatal condition prior to the onset of symptoms exists.

Preeclampsia can result in maternal complications, such as eclampsia and the HELLP syndrome (hemolysis, elevated liver enzymes, and lowered platelets). Preeclampsia can result in fetal complications such as prematurity, intrauterine growth restriction; acidosis, ongoing life challenges such as learning disorders, cerebral palsy, epilepsy, blindness, and deafness, or can even result in fetal death.

Because the pathogenesis of preeclampsia is not completely understood, prevention remains complex. Current preventative measures include diet, aspirin, physical activity, and smoke cessation.

The only known definitive treatment for preeclampsia is delivery of the fetus and placenta. The timing of delivery should balance the desire for optimal perinatal outcomes for the fetus while reducing maternal risks. The severity of disease and the maturity of the fetus are primary considerations. These considerations are situation-specific and management will vary with situation, location, and institution. Treatment can range from expectant management to expedited delivery of the fetus and placenta by induction of labor or Caesarian section, in addition to pharmaceutical interventions. Important in management is the assessment of vulnerable maternal organ systems when possible, management of severe hypertension, and prevention and treatment of eclamptic seizures. Separate interventions directed at the fetus may also be necessary.

Vasculitis

Vasculitis is thought to be an autoimmune disease that attacks blood vessels, including arteries and veins. Possible symptoms of vasculitis include fever, weight loss, palpable purpura, livedo reticularis, myalgia or myositis, arthralgia or arthritis, mononeuritis multiplex, headache, stroke, tinnitus, reduced visual acuity, acute visual loss, myocardial infarction, hypertension, gangrene, nose bleeds, bloody cough, lung infiltrates, abdominal pain, bloody stool, perforations, and glomerulonephritis.

Vasculitis can be classified by the cause, the location of the blood vessel, the type of blood vessel, or the size of the blood vessel.

Diseases such as syphilitic aortitis, or the inflammation of the aorta, is an example of one cause of vasculitis. However, the causes of many forms of vasculitis are poorly understood. There is usually an immune component, but the trigger is often not identified. In these cases, the antibody found is sometimes used in classification, for example, as in ANCA-associated vasculitides.

Vasculitis can also be classified by the location of the vessel. For example, ICD-10 classifies "vasculitis limited to skin" with skin conditions, and "necrotizing vasculopathies" (corresponding to systemic vasculitis) with musculoskeletal system and connective tissue conditions. Arteritis/phlebitis on their own are classified with circulatory conditions.

Vasculitis can also be classified by the type of vessel or the size of the vessel. For example, apart from the arteritis/phlebitis distinction mentioned above, vasculitis is often classified by the caliber of the vessel affected. However, there can be some variation in the size of the vessels affected.

Laboratory tests of blood or body fluids test patients with active vasculitis. These patients' results can generally show signs of inflammation in the body, such as increased erythrocyte sedimentation rate (ESR), elevated C-reactive protein (CRP), anemia, increased white blood cell count and eosinophilia. Other possible results include elevated antineutrophil cytoplasmic antibody (ANCA) levels and hematuria. Other organ functional tests may be abnormal. Specific abnormalities depend on the degree of various organs involvement. A BrainSPECT can show decreased blood flow to the brain and brain damage. The definite diagnosis of vasculitis is established after a biopsy of involved organ or tissue, such as skin, sinuses, lung, nerve, brain and kidney. The biopsy elucidates the pattern of blood vessel inflammation. An alternative to biopsy can be an angiogram (x-ray test of the blood vessels). It can demonstrate characteristic patterns of inflammation in affected blood vessels.

In some embodiments, SLEDAI-2K Responder Index 50 (SRI-50) descriptors characterize symptoms of vasculitis, including, but not limited to ulceration, gangrene, tender finger nodules, periungual infarction, splinter hemorrhages, or biopsy or angiogram proof of vasculitis. In some embodiments, improvement (as defined by SRI-50) can be indicated by greater than or equal to 50% improvement of the vasculitis lesions present with no new lesion or worsening in either. In some embodiments, improvement can be indicated by greater than or equal to 50% decrease in the body surface area; for periungual infarction, splinter hemorrhages or tender finger nodules a greater than or equal to 50% improvement is defined as greater than 50% decrease in the total number of involved digits with periungual infarction, splinter hemorrhages and tenderfinger nodules (for multiple lesions in a single digit, count only one).

$^{18}$F-fluorodeoxyglucose positron emission tomography/computed tomography (FDG-PET/CT) has become a widely used imaging tool in patients with suspected Large Vessel Vasculitis, due to the enhanced glucose metabolism of inflamed vessel walls. The combined evaluation of the intensity and the extension of FDG vessel uptake at diagnosis can predict the clinical course of the disease, separating patients with favorable or complicated progress. Acute onset of vasculitis-like symptoms in small children or babies may instead be the life-threatening purpura fulminans, usually associated with severe infection.

Treatments are generally directed toward preventing inflammation and suppressing the immune system. Typically, corticosteroids such as prednisone are prescribed. Additionally, other immune suppression drugs, such as cyclophosphamide and others, are considered. In case of an infection, antimicrobial agents such as cephalexin may be used. Affected organs (e.g., the heart or lungs) may require specific medical treatment intended to improve their function during the active phase of the disease.

Prediction in Autoimmune Disease

In some embodiments, provided methods and compositions may be used to determine and/or predict likely outcomes of treatment for any of a variety of aspects of the course of an autoimmune disease (e.g., lupus erythematosus, preeclampsia, vasculitis). In some embodiments, the provided methods are performed either in the absence or presence of treatment.

In some embodiments, provided methods are used to determine and/or predict the need for one or more treatments, including but not limited to, new or increased use of high dose prednisone (e.g., greater than 20 mg/day), use or increased use of immunosuppressives, and/or hospitalization. In some embodiments, provided methods are used to determine and/or predict likely outcomes of treatment of an acute increase in disease severity sufficient. In some cases, provided methods may be used to predict likely outcome of treatment prior to the occurrence of an acute increase in disease severity such that the acute increase is prevented or reduced in severity.

In some embodiments, provided methods are used to determine and/or predict a need for hospitalization due to an autoimmune disease, for example, SLE. In some embodiments, provided methods are used to determine and/or predict of the likelihood of achieving a certain score on one or more disease indices, for example the SELENA SLEDAI Flare Index or the Physician Global Assessment (PGA), for example, within the next 30 days, 60 days, or 90 days.

In some embodiments, provided methods are used to predict the occurrence of a measurable increase in disease activity in one or more organ systems involving new or worse clinical signs and symptoms and/or laboratory measurements, for example, within the next 30 days. In some embodiments, provided methods are used to predict the occurrence of a change of greater than or equal to 1.0 in the physician's global assessment of disease activity (measured on a 0-3) scale from the previous visit or from a visit within the last 200 days (e.g., last 100 days, e.g., last 93 days, e.g., last 75 days, e.g., last 50 days, e.g., last 25 days, e.g., last 10 days, e.g., last 5 days, e.g., last 1 day), for example within the next 30 days.

In some embodiments, iC3b/total C3 ratios and/or iC3b/intact C3 ratios correlate with one or more characteristics that allow for predicting the onset of increased disease activity (e.g., an episodic change of activity, e.g., flare). One who is skilled in the art will be aware of such characteristics that are used to diagnose flare. In some embodiments, characteristics that correlate with iC3b/total C3 ratios and/or iC3b/intact C3 ratios include, but are not limited to, the need for treatment, including but not limited to, new or increased use of high dose prednisone (e.g., greater than 20 mg/day), new or increased use of immunosuppressives, an acute increase in disease severity sufficient to cause a clinician to initiate or alter treatment in a subject, any hospitalization that has occurred due to SLE or death due to SLE, a certain score on one or more disease indices, for example the SELENA SLEDAI Flare Index or the Physician Global Assessment (PGA), a measurable increase in disease activity in one or more organ systems involving new or worse clinical signs and symptoms and/or laboratory measurements (where the measurable increase in disease activity is considered clinically significant by the assessor and usually there would be at least consideration of a change or an increase in treatment), or a change of greater than or equal to 1.0 in the physician's global assessment of disease activity (measured on a 0-3) scale from the previous visit or from a visit within the last 200 days (e.g., last 100 days, e.g., last 93 days, e.g., last 75 days, e.g., last 50 days, e.g., last 25 days, e.g., last 10 days, e.g., last 5 days, e.g., last 1 day).

In some embodiments, iC3b/total C3 ratios and/or iC3b/intact C3 ratios correlate with a characteristic that allows for predicting flares within hours, within days, within weeks, or within months from an initial visit. In some embodiments, flares are predicted within 10 hours, within 24 hours, within 1 day, within 2 days, within 5 days, within 1 week, within 2 weeks, within 3 weeks, within 4 weeks, within 2 months, within 4 months, within 6 months, within 10 months, within 12 months, within 2 years from an initial visit.

In some embodiments, predicting a characteristic (e.g., an episodic change of activity, e.g., flare) of autoimmune disease may include determining that the iC3b/total C3 ratios and/or iC3b/intact C3 ratios is present at a level higher than a reference level. In some embodiments, predicting flare may be correlated with and/or followed by the absence, presence, or adjustment of treatment.

The Complement System

The complement system comprises more than 50 serum and cellular proteins and plays important roles in innate and adaptive immunity. There are three major pathways of complement activation. The classical pathway is primarily activated by immune complexes, specifically IgG/IgM antibodies bound to antigen. Other activators include lipopolysaccharide, myelin, polyanionic compounds, C-reactive protein (CRP), and microbial DNA and RNA. The lectin pathway is activated by polysaccharides with free-mannose group and other sugars common to fungi and bacteria. The alternative pathway is mediated by direct C3 activation by "foreign" substances that often include microbial cell wall components. All three major pathways of complement activation converge on the central protein complement component 3 (C3). C3 is a central mediator of inflammation and is activated by most factors that cause inflammation. A schematic of the complement system is shown in FIG. 1.

The classical pathway is typically triggered by immune complexes, which are complexes of antigen bound with antibodies, generally belonging to the IgM or IgG isotypes. Immune complexes in turn bind to complement component C1, which is comprised of C1q, C1r, and C1s. The binding of C1q to an antibody-antigen complex triggers activation of C1r and C1s. Activated C1s then cleaves component C4 to produce C4a and C4b. C4b is capable of covalent attachment to cell surfaces, although only about five percent does so. The remaining 95 percent reacts with water to form a soluble, activated C4b. Component 2 can then associate with C4b, which after which it is activated by C1s to C2a and C2b. C4b and C2a combine to form C4bC2a, the classical pathway (CP) C3 convertase.

The CP convertase cleaves C3 to form C3a and C3b. Like activated C4b, C3b can covalently bind to cell surfaces or react with $H_2O$ and stay in solution. Activated C3b has multiple roles. By itself, it can serve as an opsonin to make the decorated cell or particle more easily ingested by phagocytes. In addition, C3b can associate with C4bC2a (the CP C3 convertase) to form a C5 convertase. The complex, termed C4bC2aC3b is termed the CP C5 convertase. Alternatively, C3b can form the core of another C3 convertase called the alternative pathway (AP) C3 convertase.

The alternative pathway (AP) is another mechanism by which C3 can become activated. It is typically activated by targets such as microbial surfaces and various complex polysaccharides and other materials. This alternative pathway can also be initiated spontaneously by the cleavage of the thioester bond in C3 by a water molecule to form $C3(H_2O)$. $C3(H_2O)$ binds factor B, which allows factor D to cleave factor B to Ba and Bb. Bb remains associated with $C3(H_2O)$ to form $C3(H_2O)Bb$ complex, which acts as a C3 convertase and cleaves C3, resulting in C3a and C3b.

C3b formed either via this process or via the classical or lectin pathways binds to targets (e.g., on cell surfaces) and forms a complex with factor B, which is subsequently cleaved by factor D to form Bb, resulting in C3bBb, which is termed the alternative pathway (AP) C3 convertase. Binding of another molecule of C3b to the AP C3 convertase produces C3bBbC3b, which is the AP C5 convertase.

The lectin complement pathway is initiated by binding of mannose-binding lectin (MBL) and MBL-associated serine protease (MASP) to carbohydrates. The MBL1 gene (known as LMAN1 in humans) encodes a type 1 integral membrane protein localized in the intermediate region between the endoplasmic reticulum and the Golgi. The MBL2 gene encodes the soluble mannose-binding protein found in serum. In the human lectin pathway, MASP1 and MASP2 are involved in proteolysis of C4 and C2, leading to C3 convertase, which lead to production of a C5 convertase as described above for the CP.

C5 convertase generated via any of the three pathways cleave C5 to produce C5a and C5b. C5b then binds to C6, C7, and C8, which catalyzes polymerization of C9 to form the C5b-9 membrane attack complex (MAC). The assembling MAC inserts itself into target cell membrane, forming a pore delineated by a ring of C9 molecules. MAC formation causes cell lysis of invading microbes, MAC formation on host cells can also cause lysis, but not necessarily. Sublytic amounts of MAC on the membrane of cells may affect cell function in a variety of ways. The small cleavage products C3a, C4a, and C5a are anaphylatoxins and mediate multiple reactions in the acute inflammatory response. C3a and C5a are also potent chemotactic factors that attract immune system cells such as neutrophils and macrophages into the area of crisis.

Complement C3

Complement component C3 is useful as a general alert biomarker that the body is responding to some form of physiological crisis, such as injury, infection, or other disease process. Complement has been associated with a wide variety of diseases, and, in some cases, complement can play a role in disease pathology. In these cases, the body is not able to successfully control the cause of inflammation, which goes from local to systemic. Complement activation can directly damage tissue or do so indirectly by over-activating cells and recruiting immune cells that in turn cause tissue destruction. Examples of over activation include anaphylactic shock, multiple organ failure (MOF), acute respiratory distress syndrome (ARDS), and systemic inflammatory response syndrome (SIRS).

In some embodiments, where the sample is blood, plasma or serum, a "normal" level of intact C3 may fall within the range 300 ug/ml-1,700 ug/ml; in other embodiments, a "normal" level of intact C3 may fall within the range 400 ug/ml-1,400 ug/ml; in still other embodiments, a "normal" level of intact C3 may fall within the range 500 ug/ml-1,300 ug/ml; in still other embodiments, a "normal" level of intact C3 may fall within the range 500 ug/ml-1,200 ug/ml; in still other embodiments, a "normal" level of intact C3 may fall within the range 500 ug/ml-1,100 ug/ml; in still other embodiments, a "normal" level of intact C3 may fall within the range 500 ug/ml-1,000 ug/ml; in still other embodiments, a "normal" level of intact C3 may fall within the range 500 ug/ml-900 ug/ml; in yet other embodiments, a "normal" level of intact C3 may fall within the range 500 ug/ml-800 ug/ml; in yet other embodiments, a "normal" level of intact C3 may fall within the range 500 ug/ml-700 ug/ml; in yet other embodiments, a "normal" level of intact C3 may fall within the range 500 ug/ml-600 ug/ml. As a more specific example, in some embodiments where the sample is whole blood, a "normal" level of intact C3 may fall within the range 500 ug/ml-1,000 ug/ml. As a more specific example, in some embodiments where the sample is plasma, a "normal" level of intact C3 may fall within the range 700 ug/ml-1,700 ug/ml. As a more specific example, in some embodiments where the sample is serum, a "normal" level of intact C3 may fall within the range 700 ug/ml-1,700 ug/ml.

In other embodiments, where the sample is tears, a "normal" level of intact C3 may fall within the range 30 ug-ml-100 ug/ml, in other embodiments, a "normal" level of intact C3 may fall within the range 40 ug/ml-90 ug/ml; in still other embodiments, a "normal" level of intact C3 may fall within the range 50 ug/ml-80 ug/ml; in still other embodiments, a "normal" level of intact C3 may fall within the range 50 ug/ml-70 ug/ml; in still other embodiments, a "normal" level of intact C3 may fall within the range 50 ug/ml-60 ug/ml.

In some embodiments, where the same is urine, a "normal" level of intact C3 may be 0.5 ug/ml or less (e.g., 0.4 ug/ml, 0.3 ug/ml, 0.2 ug/ml, 0.1 ug/ml or less).

In some embodiments, where the sample is blood, plasma or serum, a "normal" level of total C3 may fall within the range 300 ug/ml-1,700 ug/ml; in other embodiments, a "normal" level of total C3 may fall within the range 400 ug/ml-1,400 ug/ml; in still other embodiments, a "normal" level of total C3 may fall within the range 500 ug/ml-1,300 ug/ml; in still other embodiments, a "normal" level of total C3 may fall within the range 500 ug/ml-1,200 ug/ml; in still other embodiments, a "normal" level of total C3 may fall within the range 500 ug/ml-1,100 ug/ml; in still other embodiments, a "normal" level of total C3 may fall within the range 500 ug/ml-1,000 ug/ml; in still other embodiments, a "normal" level of total C3 may fall within the range 500 ug/ml-900 ug/ml; in yet other embodiments, a "normal" level of total C3 may fall within the range 500 ug/ml-800 ug/ml; in yet other embodiments, a "normal" level of total C3 may fall within the range 500 ug/ml-700 ug/ml; in yet other embodiments, a "normal" level of total C3 may fall within the range 500 ug/ml-600 ug/ml. As a more specific example, in some embodiments where the sample is whole blood, a "normal" level of total C3 may fall within the range 500 ug/ml-1,000 ug/ml. As a more specific example, in some embodiments where the sample is plasma, a "normal" level of total C3 may fall within the range 700 ug/ml-1,700 ug/ml. As a more specific example, in some embodiments where the sample is serum, a "normal" level of total C3 may fall within the range 700 ug/ml-1,700 ug/ml.

In other embodiments, where the sample is tears, a "normal" level of total C3 may fall within the range 30 ug-ml-100 ug/ml, in other embodiments, a "normal" level of total C3 may fall within the range 40 ug/ml-90 ug/ml; in still other embodiments, a "normal" level of total C3 may fall within the range 50 ug/ml-80 ug/ml; in still other embodiments, a "normal" level of total C3 may fall within the range 50 ug/ml-70 ug/ml; in still other embodiments, a "normal" level of total C3 may fall within the range 50 ug/ml-60 ug/ml.

In some embodiments, where the same is urine, a "normal" level of total C3 may be 0.5 ug/ml or less (e.g., 0.4 ug/ml, 0.3 ug/ml, 0.2 ug/ml, 0.1 ug/ml or less).

Complement activation in the immediate and early post-trauma period has been well documented and occurs by several different mechanisms, likely involving all three major pathways. Release and activation of proteolytic enzymes may directly activate complement components. Tissue damage and disruption of the endothelial lining expose surfaces that lack the endogenous complement inhibiting molecules that normally protect host tissues. These surfaces are susceptible to deposition of C3b and alternative pathway activation. Complement activation is also triggered by reperfusion of tissues following post-traumatic ischemia.

Multiple lines of evidence suggest that complement activation is an important factor in many of the complications of severe trauma, contributing significantly to 1/R injury, ARDS, MODS, secondary CNS injury, and sepsis. First, it is clear that complement activation is a common occurrence in the immediate post-trauma period in human trauma victims, and several studies have provided evidence suggesting that the extent of complement activation correlates positively with poor outcomes. Second, there is considerable evidence that complement activation is a major cause of I/R injury in animal models of trauma as well as in human trauma victims. Third, numerous studies have demonstrated that complement deficiency or administration of complement inhibitors reduces tissue damage and improves outcomes in a variety of experimental models including hemorrhage, ischemia/reperfusion injury, and CNS injury.

Several studies measured complement activation in trauma patients at sequential time points following severe trauma and investigated the existence of a correlation between complement activation and injury severity. Adverse outcomes such as ARDS, multi-organ failure, sepsis, and death were also monitored in relation to complement activation. In one study, complement parameters were determined over 14 days in trauma patients at risk of ARDS. All patients showed a decrease in serum levels of C3, C4, C5 and of the inhibitors C1-INH, complement factor H (CFH), and complement factor I (CFI) in the first 24 hours, indicating consumption by high levels of complement activation. See Catania et al., *Immunological consequences of trauma and shock, Ann. Acad. Med. Singapore* 28:120-32 (1999); Hecke, et al., *Circulating complement proteins in multiple trauma patients—correlation with injury severity, development of sepsis, and outcome, Crit. Care Med.* 25(12): 201524 (1997); Huber-Lang et al., *Complement-induced impairment of innate immunity during sepsis, J. Immunol.* 169:3223-31 (2002); Kang et al., *Change of complement system predicts the outcome of patients with severe thermal injury, J. Burn Care Rehabil.* 24:148-53 (2003); and Younger et al., *Detrimental effects of complement activation in hemorrhagic shock, J. Appl. Physiol.* 90:441-46 (2001).

iC3b

Figure 2:
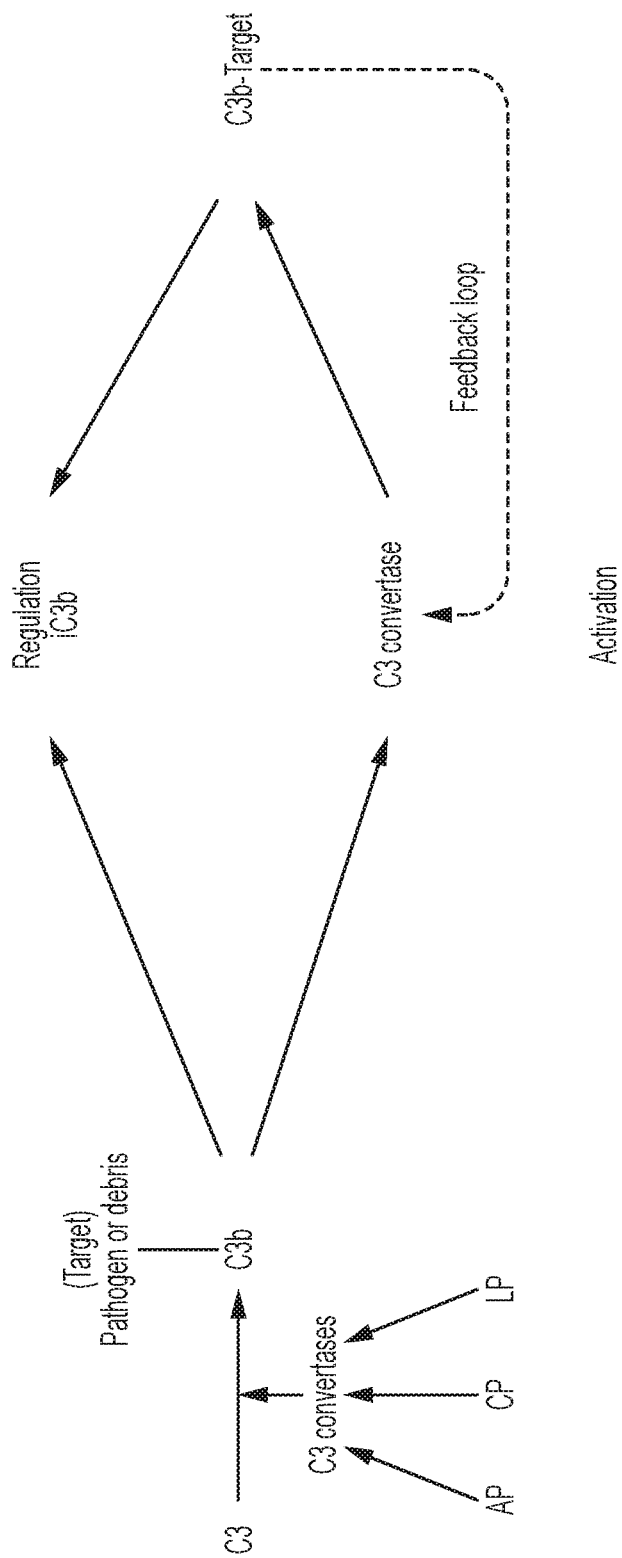
FIG. 2 shows a flow chart describing the normal flow of complement C3 activation, including the conversion of C3 into iC3b.

The iC3b protein is a breakdown product of C3, as shown in FIG. 2. The C3 breakdown product iC3b is a valuable marker of inflammatory response. iC3b has a half-life of 30 to 90 minutes, serving as a less volatile (compared to C3a), but still rapidly responsive biomarker. However, iC3b is present at much lower levels than intact or total C3 in patient samples. Thus, even a small degree of cross-talk (for example 1%) between intact C3 protein and the iC3b-specific detecting agents is very likely to produce a false positive iC3b signal at a level twice that of normal circulating iC3b. Hence, while a desirable marker of inflammation, heretofore iC3b has posed significant challenges in diagnostic testing.

In some embodiments, a "normal" iC3b level in a patient sample (e.g., bodily fluid) falls within a range with a lower boundary and an upper boundary that is higher than the lower boundary. In some embodiments, the lower boundary is selected from the group consisting of 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, 200 ng/ml, 210 ng/ml, 220 ng/ml, 230 ng/ml, 240 ng/ml, 250 ng/ml, 260 ng/ml, 270 ng/ml, 280 ng/ml, 290 ng/ml, 300 ng/ml or more. In some embodiments, the upper boundary is selected from the group consisting of 5 ug/ml, 4.5 ug/ml, 4 ug/ml, 3.5 ug/ml, 3 ug/ml, 2.5 ug/ml, 2 ug/ml, 1.9 ug/ml, 1.8 ug/ml, 1.7 ug/ml, 1.6 ug/ml, 1.5 ug/ml, 1.4 ug/ml, 1.3 ug/ml, 1.2 ug/ml, 1.1 ug/ml, 1.0 ug/ml, 0.9 ug/ml, 0.8 ug/ml, 0.7 ug/ml, 0.6 ug/ml, 0.5 ug/ml, 0.4 ug/ml, 0.3 ug/ml or less. In some embodiments a "normal" level of iC3b falls within the range of 100 ng/ml-5 ug/ml; in other embodiments a "normal" level of iC3b falls within the range of 100 ng/ml-4 ug/ml; in other embodiments a "normal" level of iC3b falls within the range of 100 ng/ml-3 ug/ml; in other embodiments a "normal" level of iC3b falls within the range of 100 ng/ml-2 ug/ml; in other embodiments a "normal" level of iC3b falls within the range of 100 ng/ml-1.5 ug/ml; in other embodiments a "normal" level of iC3b falls within the range of 200 ng/ml-1 ug/ml; in other embodiments a "normal" level of iC3b falls within the range of 200 ng/ml-0.7 ug/ml; in other embodiments a "normal" level of iC3b falls within the range of 200 ng/ml-0.5 ug/ml; in other embodiments a "normal" level of iC3b falls within the range of 200 ng/ml-0.3 ug/ml.

In some embodiments, where the sample is blood, plasma or serum, a "normal" level of iC3b may fall within the range 150 ng/ml-5,000 ng/ml; in other embodiments a "normal" level of iC3b may fall within the range 150 ng/ml-4,000 ng/ml; in other embodiments a "normal" level of iC3b may fall within the range 150 ng/ml-3,000 ng/ml; in other embodiments a "normal" level of iC3b may fall within the range 150 ng/ml-2,000 ng/ml; in other embodiments a "normal" level of iC3b may fall within the range 150 ng/ml-1,000 ng/ml; in other embodiments a "normal" level of iC3b may fall within the range 175 ng/ml-900 ng/ml; in still other embodiments a "normal" level of iC3b may fall within the range 200 ng/ml-800 ng/ml; in still other embodiments a "normal" level of iC3b may fall within the range 200 ng/ml-700 ng/ml; in still other embodiments a "normal" level of iC3b may fall within the range 200 ng/ml-600 ng/ml; in still other embodiments a "normal" level of iC3b may fall within the range 200 ng/ml-500 ng/ml; in still other embodiments a "normal" level of iC3b may fall within the range 200 ng/ml-400 ng/ml; in still other embodiments a "normal" level of iC3b may fall within the range 200 ng/ml-300 ng/ml. As a more specific example, in some embodiments where the sample is whole blood, a "normal" level of iC3b may fall within the range 10 ng/ml-1,500 ng/ml. As a more specific example, in some embodiments where the sample is plasma, a "normal" level of iC3b may fall within the range 10 ng/ml-3,000 ng/ml. As a more specific example, in some embodiments where the sample is serum, a "normal" level of iC3b may fall within the range 10 ng/ml-5,000 ng/ml.

In some embodiments, where the sample is tears, a "normal" level of iC3b may fall within the range 1 ng-ml-50 ng/ml; in other embodiments, a "normal" level of iC3b may fall within the range 1 ng/ml-40 ng/ml; in still other embodiments, a "normal" level of iC3b may fall within the range 1 ng/ml-30 ng/ml; in yet other embodiments, a "normal" level of iC3b may fall within the range 1 ng/ml-20 ng/ml; in still other embodiments, a "normal" level of iC3b may fall within the range 2 ng/ml-10 ng/ml; in yet other embodiments, a "normal" level of iC3b may fall within the range 4 ng/ml-10 ng/ml.

In some embodiments, where the sample is urine, a "normal" level of iC3b may be 0.1 ug/ml or less.

In some embodiments, iC3b is detected using a non-cross reactive antibody characterized in that a 1 ug/ul solution of intact C3 produces signal equivalent to less than about 1 ng/ml of iC3b. In some embodiments, the non-cross reactive antibody is selected from the group consisting of A209, MCA2607, and HM2199.

Complement Activation Potential (CAP)

According to various embodiments, a complement activation potential represents a likelihood of increased complement activity in a sample. In some embodiments, a complement activation potential may correlate (directly or indirectly) to a severity of inflammatory distress; the higher the complement activation potential, the greater the risk of developing inflammatory distress and/or the greater the severity of inflammatory distress experienced by the individual. In some embodiments, the complement activation potential may be expressed as a percent chance of experiencing a flare and/or adverse pregnancy outcome in the future. In some embodiments, the complement activation potential may be expressed as a percent increased or decreased risk of experiencing a flare and/or adverse pregnancy outcome in the future (e.g., within the next three months, thirty days, one week, etc.). In some embodiments, the complement activation potential may be expressed as a percent chance that currently observed signs and/or symptoms are a flare (as opposed to an infection or other cause).

In some embodiments, the complement activation potential may be expressed as a percent increase in the level of one or more complement proteins and/or ratios of complement proteins over time (either in the same or in different subjects). Examples of the expression of the complement activation potential in a sample may be found in the Examples section below, as well as throughout the specification and claims.

A complement activation potential of a sample (and thus in the subject from which it originated) may be assessed in any of a variety of ways, as provided herein. In some embodiments, a level, relationship (e.g., ratio), or change (expressed either in magnitude or percent, for example) of one or more indicators, for example, complement proteins, may be used to determine a complement activation potential in a particular subject. In some embodiments, a level, relationship, or change of one or more complement proteins may be compared against a reference level or ratio in order to determine a complement activation potential. For example, in some embodiments, the complement activation potential of a sample may be assessed for deviation from a reference value of a control (i.e., a "normal" level) which indicates complement is activated in the individual. As a further non-limiting example, in some embodiments, the level or concentration of iC3b in a sample may be elevated in comparison to a control, indicating C3 is activated and has been further split into its activation product, iC3b and thus indicating an increased complement activation potential. As a still further example, in other embodiments, the level or concentration of intact C3 in a sample is decreased in comparison to a control, indicating that intact C3 has been converted to its breakdown or activation products and is hence depleted in the individual, thus also indicating an increased complement activation potential.

In some embodiments, the level, relationship, or change of the one or more indicator(s) (e.g., complement proteins) is compared against a reference level or ratio which was obtained from the subject previously. In some embodiments, the level or ratio of the one or more indicator(s) (e.g., complement proteins) is compared against a reference level or ratio which was obtained from a different subject or population of subject (e.g., a composite score), or a normal reference range.

In some embodiments, the complement activation potential is determined through one or more of a) detecting a level of iC3b in the sample from the subject, b) determining the ratio between the levels of iC3b and total C3 in the sample from the subject, c) detecting a level of total C3 in the sample from the subject, and d) detecting the level of C4 in the sample from the subject. In some embodiments, at least two of a-d are used to determine the complement activation level in the sample. In some embodiments, provided methods include the use of one or more additional or alternative biomarkers in addition to iC3b, total C3, and C4, for example C4d.

It is specifically contemplated that many provided methods will be used to capture changes in complement activation over time in an individual (i.e., longitudinal data). In some embodiments, provided methods may be used to capture complement activation potentials in 1, 2, 5, 10 or more samples over time in order to understand the patient's inflammatory state over time. In some embodiments, provided methods are used to determine two or more complement activation potentials, each from a different sample, in a subject (e.g., 3, 4, 5, 6, 7, 8, 9, 10, 15, 20, 30, 40, 50, or more).

In some embodiments, the complement activation potential of a sample may be expressed in terms of an "odds ratio", which represents the increased chance of active disease (e.g., flare) per unit of measure for the variable(s) being assessed in a sample. Examples of this are found, inter alia, in the Examples sections below.

According to various embodiments, a complement activation potential may be used to modify the course of treatment for a subject suffering from one or more autoimmune diseases, e.g., a lupus sufferer. For example, a complement activation potential above a certain percentage may indicate the need to administer or implement a change in the treatment of a subject. In some embodiments, a treatment is administered and/or a change in treatment is implemented in a subject if the complement activation potential is about 25% or higher. In some embodiments, a treatment is administered and/or a change in treatment is implemented in a subject if the complement activation potential is about 30% or higher (e.g., 35%, 40%, 45%, 50%, 55%, 60%, 65%, 70%, 75%, 80%, 85%, 90%, 95%, 99%, 100%, 150%, 200%, 300%, 400%, 500%, or more). It is contemplated that an individual physician will apply sound medical judgment in deciding what level of complement activation potential warrants administration or a change in the treatment of an individual subject.

Types of Assays

According to various embodiments, any of a variety of assays may be used to determine a complement activation potential. In some embodiments, one or more immunoassays may be used to determine a complement activation in a sample. In some embodiments, one or more enzyme-based assays may be used to determine a complement activation in a sample. In some embodiments, one or more radioassays may be used to determine a complement activation in a sample. In some embodiments, one or more colorimetric assays may be used to determine a complement activation in a sample. In some embodiments, one or more radioimmunodiffusion assays may be used to determine a complement activation in a sample. In some embodiments, a combination of assay types are used to determine a complement activation in a sample.

By way of non-limiting example, in some embodiments, a lateral flow assay is used to determine the complement activation potential in the sample. In some embodiments, a lateral flow assay such as those described in U.S. Pat. No. 8,865,164 or U.S. Patent Application Publication 2012/0141457, the disclosures of which are hereby incorporated in their entirety, may be used.

In some embodiments, provided methods and assays allow for rapid determination of a complement activation potential which avoid problems common in many previous tests related to complement activation. For example, many previous tests for complement activation suffered from false positive results as a result of auto-activation of the complement proteins in a sample during the assay or in preparation of the sample for assay. Thus, one of the advantages of some embodiments is that the step of determining is performed under controlled conditions such that performance of the step does not substantially activate complement within the sample. In addition, some embodiments are able to provide very rapid returns of complement activation potential, such that they are amenable to point of care use. For example, in some embodiments, the complement activation level is determined within 30 minutes (e.g., within 20 minutes, within 10 minutes, within 5 minutes) of the initiation of the determining step.

Detecting Agents

According to various embodiments, any of a variety of detecting agents may be used to determine a complement activation potential. In some embodiments, a detecting agent may be one or more antibodies (e.g., monoclonal or polyclonal), antibody fragments, quantum dots, peptides, peptide-like agents, complement receptors or binding proteins, enzymes, arrays, aptamers, bead-based assay related agents, nanodrops, nanoparticles, and/or agents for use in photonic crystal enhanced fluorescence (PCEF) assays.

Samples

Any of a variety of samples may be analyzed using provided methods. In some embodiments, a sample is or comprises one or more body fluids, or is derived therefrom. In some embodiments, a sample is or comprises a body fluid selected from the group consisting of whole blood, serum, plasma, urine, tears, saliva, feces, wound exudate, pus, nasal discharge, bronchoalveolar lavage fluid, mucous secretion, sebem, sweat, semen, vaginal fluid, breast milk, breath condensate, and cerebrospinal fluid.

Treatment

As described above, there is presently no cure for autoimmune disease, including lupus. Instead, a variety of treatments are used to generally suppress the immune system and/or address signs and symptoms of the disease, and in particular flares. According to various embodiments, one or more treatments may be administered and/or the dose or other parameter of an ongoing treatment adjusted in response to a complement activation potential in a subject. In some embodiments, one or more treatments may be administered and/or adjusted if the complement activation potential in a sample increases as compared to a reference complement activation potential. In some embodiments, one or more treatments may be administered and/or adjusted if the complement activation potential in a sample increases as compared to a reference level from the same subject.

In some embodiments, administering or implementing a change in treatment results in a decrease in complement activation potential in the subject. In some embodiments, the subject does not experience a flare and/or adverse pregnancy outcome within 30 days of the administering or implementing a change in treatment.

According to various embodiments, treatment may result in a decrease in the complement activation potential in a subject. In some embodiments, the decrease in complement activation potential occurs within one month from the administration or implementation step (e.g., within three weeks, within two weeks). In some embodiments, the decrease in complement activation potential occurs within one week from the administration or implementation step (e.g., within six days, within five days, within four days, within three days, within two days, within one day).

In some embodiments, the at least one treatment is selected from the group consisting of steroids, non-steroidal anti-inflammatory drugs (NSAIDs), hydroxychloroquine, chloroquine, quinacrine, methotrexate, azathioprine, sulfasalazine, cyclophosphamide, chlorambucil, cyclosporine, mycophenolate mofetil, mycophenolate sodium, rituximab, belimumab, complement inhibitors, plasmapheresis, physical therapy, sleep therapy, and cognitive behavioral therapy. In some embodiments, the at least one treatment is or comprises part of a combination therapy administered to the subject.

According to various embodiments, provided methods allow for the prediction of flares in sufferers of autoimmune disease, for example, lupus sufferers. This invention provides the first known methods of predicting flare in, e.g., lupus sufferers, and, as such, provides the opportunity for new paradigms in the treatment of autoimmune disease. In some embodiments, a flare may be predicted between 1 and 3 months before it occurs (e.g., 1 month, 1.5 months, 2 months, 2.5 months). In some embodiments, a flare may be predicted between 1 and 4 weeks before it occurs (e.g., 1 week, 1.5 weeks, 2 weeks, 2.5 weeks, 3 week, 3.5 weeks). In some embodiments, a flare may be predicted between 1 and 7 days before it occurs (e.g., 2 days, 3 days, 4 days, 5 days, 6 days).

In addition, provided methods also allow for the prediction of adverse pregnancy outcomes, for example, in lupus suffering women. Thus, in some embodiments, provided methods allow for new paradigms in the treatment of adverse maternal and fetal complications such as preeclampsia. In some embodiments, an adverse pregnancy outcome may be predicted between 1 and 3 months before it occurs (e.g., 1 month, 1.5 months, 2 months, 2.5 months). In some embodiments, an adverse pregnancy outcome may be predicted between 1 and 4 weeks before it occurs (e.g., 1 week, 1.5 weeks, 2 weeks, 2.5 weeks, 3 week, 3.5 weeks). In some embodiments, an adverse pregnancy outcome may be predicted between 1 and 7 days before it occurs (e.g., 2 days, 3 days, 4 days, 5 days, 6 days).

EXAMPLES

Example 1—Complement Activation Signatures in Systemic Lupus Erythematosus (SLE)

In this example, the levels of certain complement proteins and ratios between complement proteins were assessed to determine if higher levels and/or ratios indicated an increased likelihood that the patient/subject was experiencing active disease (i.e. a flare).

Study Design

For this study, 111 adult patients with a validated diagnosis of SLE (assessed by the 1997 ACR criteria for classification of SLE or SLICC classification criteria for SLE) from the SLE Clinic at Washington University were enrolled. 239 patient visits were included for longitudinal analysis. Exclusion criteria included those with blood borne infectious diseases (i.e. Hep B or C, HIV), cirrhosis, ESRD, or who were pregnant. SLE disease activity was measured by the SLEDAI 2K Responder Index-50 (S2K RI-50) instrument. The S2K RI-50 is an accepted measure of SLE disease activity and is an index that measures overall disease activity through an assessment of various organs and tissues in the body. For the purposes of this example, patients having a S2K RI-50 score>4 were considered as having active disease.

The concentration of the following complement proteins and ratios of complement proteins were assessed in this example: iC3b, total C3, C4, and the ratio between C3b and total C3. In addition to these measures, the concentrations of double stranded DNA antibodies (dsDNA Ab), erythrocyte sedimentation rate (ESR), and C-reactive protein (CRP) were also measured. Two other variables were also considered in this example. The first is whether or not a particular subject was taking prednisone or not, and the second was whether the subject was Caucasian or African American.

One advantage of assaying iC3b is that the molecule is strongly indicative of active complement consumption since the serum half-life of the iC3b molecule is only 30-90 minutes. In this study, the ratio of iC3b to total C3 was also assessed because it was thought that this ratio would provide a good measure of complement consumption relative to production, thus potentially providing a more accurate picture of complement activation than through use of a single indicator. A general flow chart of the breakdown of C3 into iC3b is found in FIG. 2.

Statistical Analysis

Univariate and multivariable analyses were performed using the mixed-effects logistic regression model (Proc Glimmix in SAS version 9.4). iC3b, total C3, C4, ESR, CRP, dsDNA values along with prednisone usage and race were predictor variables used for analysis. Odds ratio and 95% confidence intervals are reported to quantify the relationship between S2K RI-50 and predictor variables.

Results

As is shown in Table 1 below, the average age of the patients in this study was just over 40 years and approximately 88% of the study participants were female with an average S2K RI-50 score of more than 5.

TABLE 1

Characteristics of Study Patients

| Age (average) ± SD | 40.8 ± 13.0 | African-American (%) | 61.1 | Prednisone (%) | 40.1 |
|---|---|---|---|---|---|
| S2K RI-50 score (average) ± SD | 5.23 ± 5.84 | White (%) | 38.9 | Prednisone dose (average) ± SD | 15.57 ± 13.97 |
| | | Female (%) | 88.7 | | |

From this patient population, as shown in Table 2 below, it was determined that the levels of iC3b and the ratio of iC3b to total C3 where strongly correlated with active disease (i.e., flare). In univariate mixed-effect logistic regression analysis, adjusting for multiple visits per patient, iC3b, iC3b/total C3 ratio, total C3, C4, dsDNA Ab, ESR, and prednisone use each predicted S2K RI-50 scores in a statistically significant manner, while CRP and race did not. In particular, for each increase of 1 ug/ml in iC3b, a patient was 29% more likely to be experiencing active disease. Also, for each increase of 0.01 in the ratio of iC3b to total C3, a patient was approximately 27% more likely to be experiencing active disease.

TABLE 2

Association of increased levels of certain complement proteins and ratio of iC3b/total C3 with disease activity

| Predictor Variable | Odds ratio | Lower 95% CI | Upper 95% CI |
|---|---|---|---|
| iC3b (Δ1 μg/mL) | 1.29 | 1.09 | 1.52 |
| iC3b/C3 ratio (Δ0.01 units) | 1.27 | 1.12 | 1.45 |
| C3 (Δ10 mg/dL) | 0.84 | 0.76 | 0.94 |
| C4 (Δ10 mg/dL) | 0.60 | 0.42 | 0.86 |
| dsDNA Ab (Δ10 IU/mL) | 1.05 | 1.02 | 1.07 |
| ESR (Δ10 mm/hr) | 1.19 | 1.04 | 1.38 |
| CRP (Δ10 mg/L) | 1.11 | 0.85 | 1.45 |
| Prednisone (Yes vs No) | 2.89 | 1.48 | 6.64 |
| Race (White vs AA) | 0.88 | 0.42 | 1.82 |

Prednisone use at any point during the study independently predicted higher S2K RI-50 scores (2.19 units higher than those never on prednisone). Therefore, we performed a separate analysis of all who had received prednisone at least once during the study to evaluate the predictive nature of iC3b and total C3. The results are shown below in Table 3.

TABLE 3

Association of increased levels of certain complement proteins and ratio of iC3b/total C3 with disease activity in prednisone users

| Predictor Variable | Odds ratio | Lower 95% CI | Upper 95% CI |
|---|---|---|---|
| iC3b (Δ1 μg/mL) | 1.28 | 1.01 | 1.64 |
| iC3b/C3 ratio (Δ0.01 units) | 1.36 | 1.12 | 1.66 |
| C3 (Δ10 mg/dL) | 0.79 | 0.68 | 0.92 |
| C4 (Δ10 mg/dL) | 0.58 | 0.34 | 0.98 |
| dsDNA Ab (Δ10 IU/mL) | 1.10 | 1.02 | 1.18 |
| ESR (Δ10 mm/hr) | 1.30 | 0.99 | 1.70 |
| CRP (Δ10 mg/L) | 1.39 | 0.75 | 2.57 |
| Race (White vs AA) | 1.23 | 0.40 | 3.77 |

In univariate mixed-effect logistic regression analysis adjusting for multiple visits per patient, iC3b, iC3b/total C3 ratio, total C3, C4, and dsDNA Ab each predicted S2K RI-50 scores in a statistically significant manner, while ESR, CRP and race did not. In particular, for each increase of 0.01 in the ratio of iC3b to total C3, the odds of the patient experiencing active disease increased by 36%. Also, for each increase of 1 ug/ml in iC3b, the odds of the patient experiencing active disease increased by 28%. Notably, in a multiple mixed-effect logistic regression analysis, only iC3b/total C3 ratio was predictive in the final model, the chance of the patient suffering from active disease increasing by 36% for each 0.01 unit increase in the iC3b to total C3 ratio.

This example shows that certain complement proteins and/or ratios between those proteins provide a new and powerful diagnostic tool in not only diagnosing disease, but also potentially in predicting the onset of a flare. Such predictive power was previously unknown and allows for new and more effective treatment for lupus sufferers.

Example 2—Longitudinal Assessment of Complement Activation Signatures in Systemic Lupus Erythematosus (SLE) Patients In this example, a longitudinal tracking of the levels and ratios of complement proteins, as well as other measures such as ESR and CRP levels are performed in lupus patients. In order to further validate the predictive power of the assessment of complement activation, this example describes a study examining the levels of complement proteins including iC3b and total C3 in lupus patients over an extended period of time.

In this study, at least 103 patients are recruited. Patients in this study will be required to have a diagnosis of SLE as defined either by the 1997 ACR criteria for the classification of SLE or the SLICC classification criteria for SLE. In addition, analysis will only be performed on patients who record at least 3 visits.

At each visit, blood samples will be taken the levels of each of iC3b, total C3, and C4 will be determined, among other measures as shown in Table 4 below, which shows a potential battery of assessments performed over multiple visits. Importantly, though table 4 shows 5 visits, it is contemplated that subjects will be followed for more than 5 visits, and the purpose of Table 4 is simply to provide an exemplary experimental design for illustrative purposes. In addition to the levels of each protein or other measure, the ratio of iC3b to total C3 will also be determined at each visit.

In addition to the blood draws each patient is asked to complete a symptoms diary each day. Alternatively or additionally, at each visit, a physician will also assess the subject for the presence of flare. The results of the blood tests are correlated with the symptoms diary to determine the predictive power of these measures.

TABLE 4

Exemplary Experimental Design

| | Visit one | Visit two | Visit three | Visit four | Visit 5 |
|---|---|---|---|---|---|
| iC3b | | | | | |
| Total C3 | | | | | |
| C4 | | | | | |
| C4d | | | | | |
| ESR | | | | | |
| dsDNA | | | | | |
| kidney tests | | | | | |
| Urine iC3b/ total C3 | | | | | |
| CMP | | | | | |
| CBC | | | | | |
| Urinalysis with microscopic analysis | | | | | |
| Spot urinary protein/creatinine ratio | | | | | |
| 25-hydroxy vitamin D | | | | | |
| Aldolase | | | | | |
| Creatine kinase | | | | | |

It is expected that increased blood and/or urine levels of iC3b and/or increased iC3b to total C3 ratios will indicate that the patient will experience a flare sometime in the coming days, weeks, or even months. The data produced in this example will allow for new paradigms in the treatment of lupus and bring new hope to patients.

Example 3—Prediction of Pregnancy Outcome in Patients with SLE

In this Example, provided methods are used to determine likely pregnancy outcomes in patients with at least one of SLE or Antiphospholipid Antibody Syndrome (APS). SLE is described above, and Antiphospholipid Antibody Syndrome (APS) is an autoimmune disorder in which the body recognizes certain normal components of blood and/or cell membranes as foreign substances and produces antibodies against them. Patients with these antibodies may experience blood clots, including heart attacks and strokes, and miscarriages. APS may occur in people with systemic lupus erythematosus, other autoimmune diseases, or in otherwise healthy individuals. APS is also known as APLS, APLA, Hughes Syndrome or "Sticky Blood." Women with APS may have difficulties with pregnancy. During pregnancy, women are at higher risk of developing blood clots and preeclampsia. In APS, pregnancies are thought to be lost because blood clots form in the placenta and starve the baby of nutrition. Some women may have trouble getting pregnant, while others may experience repeated miscarriages. Blood clots that develop in the placenta can cause fetal growth problems, fetal distress, preterm birth, or pregnancy loss. Both SLE and APS are known to correlate with a higher risk of adverse pregnancy outcome (APO).

Patients in this Example were grouped and analyzed according to the presence or absence of antiphospholipid, (aPL), antibodies and preexisting SLE. The patients were followed regularly during the course of the pregnancy, and medical and obstetrical information as well as serial blood specimens for complement and cytokine assays were collected.

In this Example, a total of 94 pregnant women with ≥4 ACR SLE criteria and/or antiphospholipid (aPL) antibodies and healthy pregnant controls (HC) were enrolled. Patients were considered aPL positive if anticardiolipin (aCL) and/or anti-β 2 Glycoprotein 1 (antiβ2GP1) were ≥40 IU IgG or IgM and/or LA was positive in ≥2 determinations with at least once during pregnancy. Exclusion criteria were multifetal pregnancy, prednisone >20 mg/d, proteinuria >1 gm/24 hr, and creatinine >1.2 mg/dL. APOs were defined as fetal death, neonatal death, preterm delivery <36 weeks due to preeclampsia or placental insufficiency, and/or growth restriction <5th percentile. Fifty four SLE patients (18 with APO and 36 without) and 40 HCs were included in this study. C3 and iC3b were measured once per trimester in serial samples from maternal plasma. Data were log transformed and analyzed (GraphPad Prism 6).

The inclusion and exclusion crieteria for this Example are set out on Table 5 below:

TABLE 5

Inclusion and Exclusion Criteria

| Inclusion Criteria | Exclusion Criteria |
|---|---|
| Patient pregnant with live intrauterine pregnancy, as defined by positive test for elevated beta-human chorionic gonadotropin (β-HCG), but ≤12 weeks by gestation (for subjects without aPL antibodies) and ≤18 weeks (for subjects with aPL antibodies) | Diabetes mellitus (Type I and Type II) antedating pregnancy |
| | Multiple fetal gestations |
| | Known or suspected hereditary complement deficiency (defined by CH50 = 0) |
| Patient between the ages of 18-45 and able to give informed consent, or age <18 years with parental consent | |
| Hematocrit >26% | |
| For APL positive: | |
|     aCL: IgG >= 4 0 GPL units; | |
|     IgM >= 40 MPL units | |
|     Positive lupus anticoagulant (LAC), Russell's Viper Venom Test(RVVT), Kaolin, dilute TTI or partial thromboplastin time lupus anticoagulant (PTT LA) | |
|     Anti-β2GPI: IgG >= 40 GPL units; IgM >= 40 MPL units | |
| For control subjects: | |
|     At least one successful pregnancy | |
|     No history of fetal death (death of conceptus ≥10 weeks' gestation) | |
|     No more than 1 miscarriage <10 weeks' gestation | |
|     No history of positive aPL in local lab or positive aPL in core labs at screening | |
|     Not currently a smoker | |
|     No medical problems requiring chronic treatment | |

For the purposes of data analysis, patients were designated as being in one of four Groups, as outlined in Table 6 below:

TABLE 6

Group Definitions

| Group/Cohort | Definition |
| --- | --- |
| Group 1 (aPL +/SLE−) | Positive antiphospholipid antibodies (aPL) defined as positive LAC and/or anti cardiolipin IgG/IgM >= 40 units and/or anti-beta 2 glycoprotein I IgG or IgM >= 40 units; no SLE |
| Group 2 (aPL +/SLE+) | Positive antiphospholipid antibodies (aPL) defined as positive LAC and/or anti cardiolipin IgG/IgM >= 40 units and/or anti-beta 2 glycoprotein I IgG or IgM >= 40 units AND SLE defined as four or more American College of Rheumatology criteria for SLE. |
| Group 3 (aPL −/SLE+) | No antiphospholipid antibodies; SLE defined as four or more American College of Rheumatology criteria for SLE. |
| Group 4 (Apl −/SLE−) | Healthy controls: no antiphospholipid antibodies; no SLE |

Results

Figure 3:
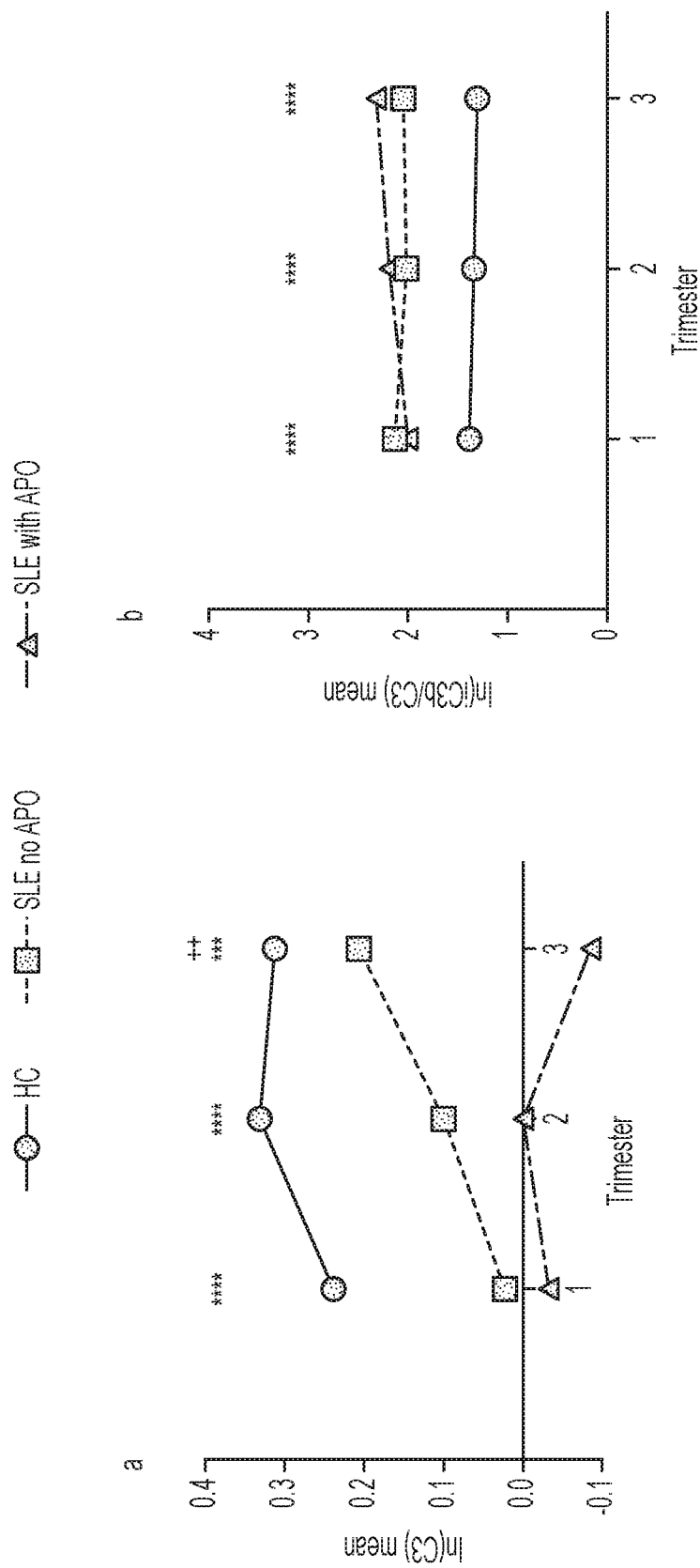
FIG. 3 panel a shows an exemplary graph of average levels of total C3 over the course of pregnancy in healthy controls (HC), women suffering from SLE that did not experience an adverse pregnancy outcome (APO), and women suffering from SLE that did experience an APO. Panel b shows an exemplary graph of average iC3b/total C3 ratios over the course of pregnancy in the same populations as in panel a. "ln" stands for natural log.
Figure 4:
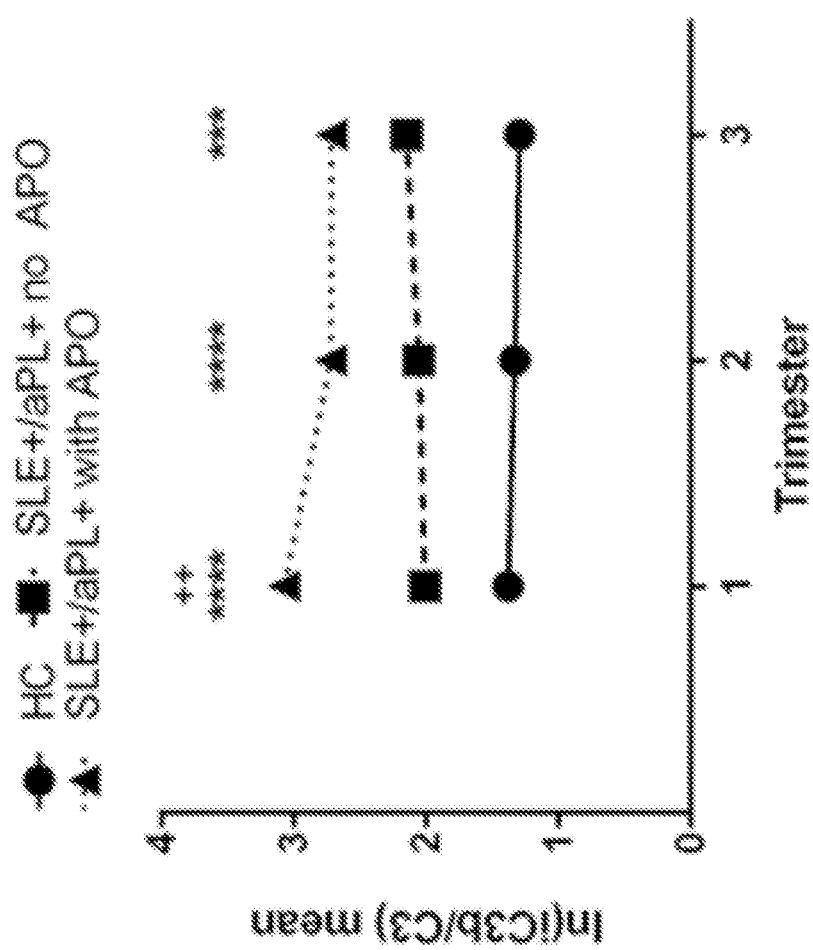
FIG. 4 shows an exemplary graph of average levels of iC3b/total C3 over the course of pregnancy in healthy controls, women suffering from SLE and had antiphospholipid (aPL) antibodies in their blood who experienced an APO, and women suffering from SLE and had aPL antibodies in their blood who did not experience an APO. "ln" stands for natural log.

Compared with healthy controls, patients with SLE had lower C3, higher iC3b levels, and elevated iC3b/total C3 ratios throughout pregnancy (FIG. 3), **$p<0.0001$, $p<0.001$*, Tukey's post-hoc++). Although neither C3 nor iC3b early in pregnancy predicted APO (FIG. 3b), total C3 levels were lower in the 3rd trimester in SLE with late APOs (n=13) compared with uncomplicated SLE and HC pregnancies (n=41) (FIG. 3a. ANOVA: F=9.213, $P<0.001$, Tukey's post-hoc). In the subset of aPL-positive SLE patients (n=13), elevated iC3b/C3 ratios were associated with APOs (n=5) (FIG. 4, ANOVA: F=19.48, **$p<0.0001$, $p<0.001$*, Tukey's post-hoc++).

In this Example, it is shown that levels of iC3b, total C3, or iC3b/total C3 ratios may be used to predict a likelihood of adverse pregnancy outcome. In this Example, women in either or both aPL or SLE groups were assessed, though it is likely that this predictive power of one or more of these measures is not so limited. In particular, lack of an increase in circulating total C3 levels as pregnancy proceeds was associated with late adverse pregnancy outcome.

Example 4—Whole Blood iC3b Concentration as Predictor of SLE Flare

In this Example, provided methods are used to determine whether iC3b concentration can be used to determine flare from non-flare visits.

In this Example, 159 patients with SLE (according to 1997 ACR criteria for the classification of SLE or 2012 SLICC classification criteria for SLE) were enrolled in the Lupus Clinic at Washington University in St. Louis and followed longitudinally in the course of their routine clinical care, totaling 327 visits. In this Example, 11 visits were removed due to no S2kRI50 disease activity score (n=9) or no iC3b result (n=2). One patient was removed due to missing iC3b value at their single visit. In this Example, the patients were followed from a few weeks to about two years, with from about 120 to about 140 days between visits.

In this Example, SLE flare was defined based on published literature and clinical experience of the investigators as a time point characterized by one or more of the following: a) new or increased use of high dose prednisone (>20 mg/day); b) new or increased use of immunosuppressives; and/or c) hospitalization due to SLE or death due to SLE.

At each visit, whole blood was drawn into plasma-EDTA tubes alongside standard of care clinical labs, diluted into sample management buffer, and whole blood iC3b concentration was measured by COMPACT® iC3b testing system (Kypha, Inc. St. Louis, Mo.) according to the instructions for use (IFU).

Figure 5:
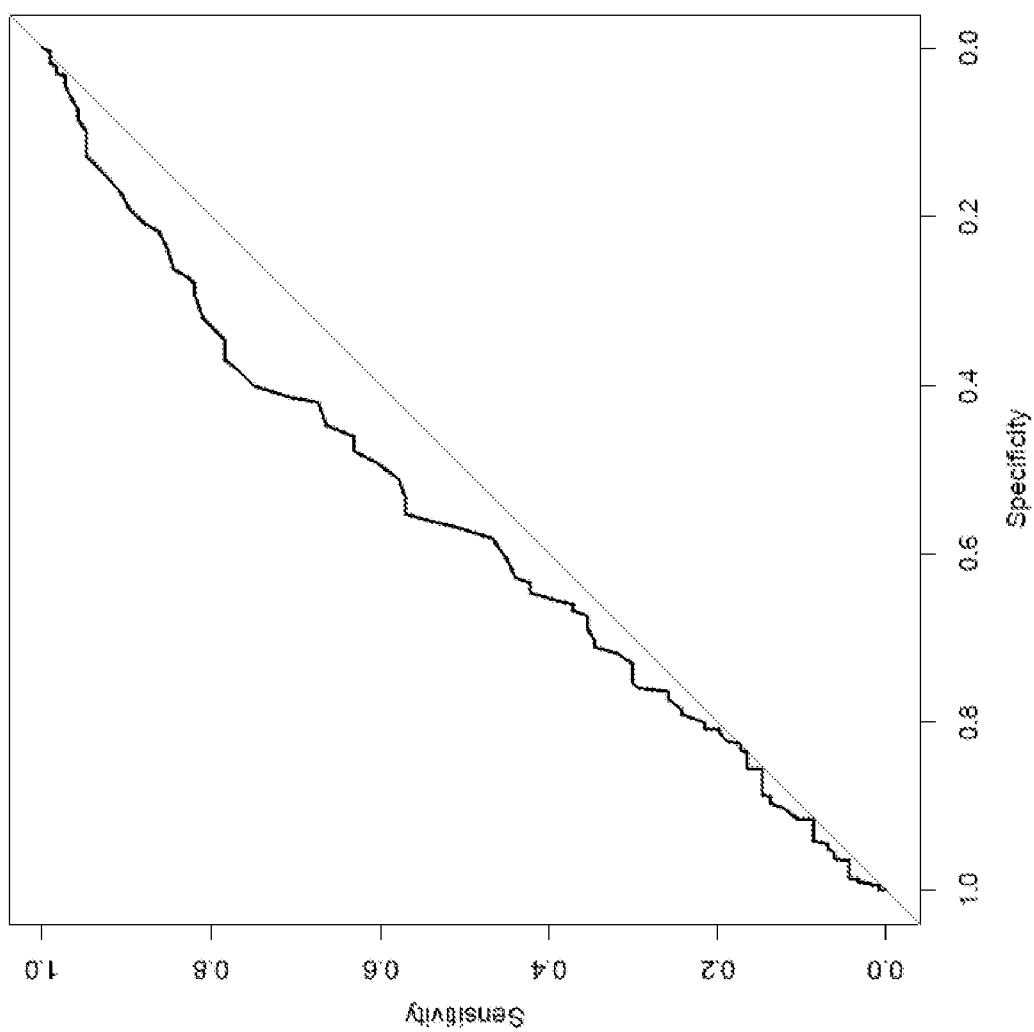
FIG. 5 shows a receiver operating characteristics (ROC) analysis that indicates that whole blood iC3b concentration can be used as a predictor of SLE flare.

As shown in FIG. 5, a receiver operating characteristics (ROC) analysis was performed to determine whether iC3b concentration could determine flare from non-flare visits. In this analysis, area under the curve (AUC) is reported to be above 0.5, which indicates that the test was able to distinguish between flare and non-flare visits. The AUC for iC3b in the dataset used to depict FIG. 5 is 0.564. In this Example, these patients were followed longitudinally and the pilot dataset includes a variable number of visits per patient. As a result, the analysis was adjusted to account for repeated measures. The adjusted 95% confidence interval (CI) that accounts for repeated measures (clusters) in the dataset is given by (0.5018, 0.6271). A 95% CI that remains above 0.5 provides that iC3b concentration can be used to distinguish SLE flare from non-flare. Without wishing to be held to a particular theory, it is contemplated that assessment of iC3b and/or ratios of iC3b and total C3 may be used to predict flare before the occurrence of the flare or during a subacute manifestation of the early stages of flare, for example, to allow a physician to prevent the occurrence of a flare or to reduce the severity of the flare if it occurs.

Example 5—A Longitudinal Study of SLE

In this Example, provided methods are used to determine at least any of the following: active SLE outcome, an analysis of clinical changes in SLE activity, and a growth curve model of S2K RI-50>4.

In this Example, data was collected from 157 patients with from 1 to 10 visits and is presented in the Tables below. For example, four patients had 8 visits and two patients had 9 and 10 visits, respectively. In this Example, a multilevel logistic regression (Proc Glimmix in SAS version 9.4) was used to examine relationships between SLE activity (defined as S2K RI-50>4) and biomarkers and prednisone treatment (however, note that other types of treatments could be examined, combinations of treatments could be examined, or effects without treatment could be examined). The clinical improvement status (flarevar variable) was assessed after a patient's first visit at the clinic. The clinical improvement status includes improved, unchanged, and worsening based on the change of S2K RI-50 scores between adjacent visits. In this Example, this outcome variable was treated as an ordinal variable. The multilevel multinomial logistic regression with generalized estimating equation (GEE) was applied to examine the relationships between the clinical status and predictor variables using Proc GENMOD in SAS version 9.4. To calculate the iC3b/total C3 ratio, C3 unit was divided by 100 to converted mg/dL to mg/mL and then the iC3b/total C3 ratio was calculated. However, note that the main effect of total C3 is in the mg/dL unit.

Active SLE Outcome

Table 7 shows the multilevel multiple logistic regression results from the data collected and analyzed as described above. As shown in Table 7, for every 1 unit increase in iC3b/total C3 ratio, an individual patient's odds of having active SLE increases by 19% when dsDNA and prednisone treatment status were held constant, as indicated by the odds ratio (OR) column in Table 7.

TABLE 7

Multilevel multiple logistic regression analysis of S2K RI-50 > 4 predicted by significant independent variables based on 445 observations among 153 patients during their 8 visits

| Predictor Variable | OR | Lower 95% CI | Upper 95% CI | p-value for Beta (OR) |
|---|---|---|---|---|
| iC3b/C3 ratio (Δ 1 unit) | 1.19 | 1.06 | 1.34 | 0.004 |
| dsDNA (Δ 10 IU/mL) | 1.03 | 1.01 | 1.05 | 0.006 |
| Prednisone (Yes vs. no) | 3.14 | 1.58 | 6.23 | <0.001 |
| Intercept variance | 1.99 | | | 0.018 |

Note:
iC3b/C3 ratio = 100 * iC3b/total C3.

This analysis shows, among other things, that the probability of having active SLE is increased as a function of increasing iC3b/C3 ratio while other laboratory values for complement components (total C3 and C4) and other tests (i.e. ESR) were not significant. Prednisone treatment stratified this patient population since it is prescribed to patients experiencing clinically significant disease activity. As a result, iC3b and C3 results were stratified is subsequent sub-analyses.

In this Example, parallel analyses were conducted among patients who received prednisone treatment. However, parallel analyses can also be conducted among patients who received other forms of treatment (e.g., immunosuppressives), or among patients who did not receive any treatment, or among patients who received combinations of treatment.

When multiple variables were jointly examined in the same model in patients receiving prednisone treatment, iC3b, which was separately tested from iC3b/C3 ratio, was statistically significant after adjusting for the effects of C3, as shown in Table 8. Other variables were not significant and were dropped from the final model. Specifically, for every 1 μg/mL increase in iC3b, an individual patient's odds of having active disease increased by 32% when C3 was held constant. Without wishing to be held to a particular theory, it is possible that controlling for total C3 level allows for more specific assessment of complement protein consumption, as opposed to overall production. Similarly, for every 10 mg/dL increase in total C3, a patient's odds of having active disease decreased by 2% (=1−0.98) when iC3b was held constant. The variance for the random intercept was not statistically significant, which indicates that the patient's initial status of SLE activity was about the same.

TABLE 8

Multilevel multiple logistic regression analysis of S2K RI-50 > 4 among 73 patients who received prednisone treatment.

| Predictor Variable | OR | Lower 95% CI | Upper 95% CI | p-value for Beta (OR) |
|---|---|---|---|---|
| iC3b (Δ1 μg/mL) | 1.32 | 1.10 | 1.59 | 0.004 |
| C3neph (Δ10 mg/dL) | 0.98 | 0.96 | 0.99 | 0.001 |
| Intercept variance | 1.06 | | | 0.14 |

Among patients receiving prednisone treatment, increasing iC3b concentration was significantly associated with increased odds of disease activity. As a result, it may be possible to use iC3b values to monitor response to prednisone or other treatments and discontinue their usage as iC3b values decrease.

When iC3b/C3 ratio was included in a multiple logistic regression model with other covariates, iC3b/C3 ratio was the only significant predictor for S2K RI-50>4 (as shown in Table 9). The variance for the random intercept was not statistically significant.

TABLE 9

Multilevel multiple logistic regression analysis of S2K RI-50 > 4 among 73 patients who received the prednisone treatment

| Predictor Variable | OR | Lower 95% CI | Upper 95% CI | p-value for Beta (OR) |
|---|---|---|---|---|
| iC3b/C3 Ratio (Δ1 unit) | 1.20 | 1.03 | 1.39 | 0.02 |
| C3neph (Δ10 mg/dL) | 0.99 | 0.97 | 1.01 | 0.18 |
| Intercept variance | 1.20 | | | 0.13 |

Among patients receiving prednisone treatment, increasing iC3b/total C3 ratio was similarly associated with increased odds of disease activity. As a result, it may be possible to use iC3b/C3 ratio values to monitor response to prednisone or other treatments and discontinue their usage as iC3b/C3 ratio values decrease.

Analysis of Clinical Changes in SLE Activity

In this Example, a total of 108 patients with the number of visits from 2 to 10 were included in analyzing clinical changes in SLE activity over time (between clinic visits). Table 10 shows that iC3b/total C3 ratio was inversely associated with the clinically meaningful improvement. For every 1 unit increase in the ratio, the average odds of getting clinically meaningful improvement was reduced by 6% (=1−0.94) in this patient population. Erythrocyte sedimentation rate (ESR) was also inversely associated with the clinically meaningful improvement. The remaining predictor variables were not statistically significant.

TABLE 10

Univariate cumulative logistic regression analysis with Generalized Estimating Equations (GEE) for the flare outcome

| Predictor Variable | N Visits | OR | Lower 95% CI | Upper 95% CI | p-value for Beta (OR) |
|---|---|---|---|---|---|
| Wb_iC3b (Δ 1 μg/mL) | 296 | 0.93 | 0.85 | 1.02 | 0.14 |
| iC3b/C3 ratio (Δ 1 unit) | 296 | 0.94 | 0.92 | 0.97 | <0.0001 |
| C3neph (Δ 10 mg/dL) | 306 | 1.04 | 0.97 | 1.13 | 0.27 |
| C4neph (Δ 10 mg/dL) | 306 | 1.07 | 0.85 | 1.36 | 0.54 |
| ESR (Δ 10 mm/hr) | 301 | 0.92 | 0.85 | 0.996 | 0.04 |
| CRP (Δ 10 mg/L) | 301 | 0.87 | 0.69 | 1.09 | 0.22 |
| dsDNA (Δ 10 IU/mL) | 306 | 0.998 | 0.98 | 1.01 | 0.77 |
| Any medication (e.g., azathioprine, methotrexate, mycophenolate mofetil, and prednisone) | 305 | 1.26 | 0.76 | 2.09 | 0.38 |
| Prednisone (Yes vs. no) | 304 | 0.81 | 0.55 | 1.19 | 0.29 |

In this univariate analysis, only iC3b/total C3 ratio and ESR were significantly associated with detecting dynamic changes in SLE disease activity between patient visits. Patients who had increases in iC3b/C3 ratio were less likely to be improving in their clinical courses.

In this Example, when all variables were included in a multiple cumulative logistic regression model, iC3b/total C3 ratio, dsDNA and prednisone variables were statistically significant. ESR was no longer significant in the multiple regression model. The estimates from the final model are depicted in Table 11. The odds ratios (OR) were adjusted for all variables in Table 11. The average odds (in this patient population) of getting clinically meaningful improvement in disease activity decreased by 10% for every unit increase in iC3b/C3 ratio when dsDNA and prednisone treatment on the SLE flare activity were held constant. Equivalently, the average odds (in this patient population) of getting worse in disease activity increased by 11% (=1/0.9) for every unit increase in iC3b/C3 ratio after adjustment for the effects of dsDNA and prednisone treatment on the SLE flare activity. The average odds (in this population) of getting clinically meaningful improvement increased by 2% for every 10 IU/mL increase in dsDNA when other variables were held constant. The average odds (in this population) of getting clinically meaningful improvement for the prednisone treatment group was 1.5 times the odds for the non-prednisone treatment group when other variables were held constant.

TABLE 11

Multiple cumulative logistic regression analysis with GEE for the flare outcome predicted by significant predictors in 137 patients with a total of 238 visits

| Predictor Variable | Adjusted OR | Lower 95% CI | Upper 95% CI | p-value for Beta (OR) |
|---|---|---|---|---|
| iC3b/C3 ratio (Δ 1 unit) | 0.90 | 0.86 | 0.95 | <0.0001 |
| dsDNA (10 IU/mL) | 1.02 | 1.003 | 1.03 | 0.034 |
| Prednisone (Yes vs. no) | 1.50 | 1.03 | 2.19 | 0.016 |

Only changes in iC3b/total C3 ratio remained significantly associated with dynamic changes in disease activity when other laboratory values were taken into account in this multivariate analysis. Additionally, the relationship between dsDNA and prednisone treatment status became significant when other parameters were taken into account.

As described above, in this Example parallel analyses were performed in patients who received prednisone treatment at any point during the study. Table 12 shows the results from the univariate analyses that examine the change in SLE activity and each predictor variable separately. The whole blood iC3b and iC3b/C3 ratio were statistically significant predictor of the flare outcome variable. The average odds (in this patient population) of getting improved in flare decreased by 17% for every unit increase in the whole blood iC3b. Equivalently, the average odds (in this patient population) of getting worse in flare activity increased by 12% for every unit increase in whole blood iC3b. The average odds (in this patient population) of getting improved in flare activity decreased by 7% for every unit increase in iC3b/total C3 ratio. Equivalently, the average odds (in this patient population) of getting worse in flare activity increased by 8% for every unit increase in iC3b/C3 ratio.

TABLE 12

Univariate cumulative logistic regression analysis with GEE for the flare outcome in 44 patients who received the prednisone treatment at any visit

| Predictor Variable | N | OR | Lower 95% CI | Upper 95% CI | p-value for Beta (OR) |
|---|---|---|---|---|---|
| Wb_iC3b (Δ 1 μg/mL) | 131 | 0.85 | 0.76 | 0.95 | 0.006 |

TABLE 12-continued

Univariate cumulative logistic regression analysis with GEE for the flare outcome in 44 patients who received the prednisone treatment at any visit

| Predictor Variable | N | OR | Lower 95% CI | Upper 95% CI | p-value for Beta (OR) |
|---|---|---|---|---|---|
| iC3b/C3 ratio (Δ 1 unit) | 131 | 0.93 | 0.90 | 0.96 | <0.0001 |
| C3neph (Δ 10 mg/dL) | 134 | 1.07 | 0.97 | 1.18 | 0.56 |
| C4neph (Δ 10 mg/dL) | 134 | 1.10 | 0.81 | 1.51 | 0.53 |
| ESR (Δ 10 mm/hr) | 132 | 0.85 | 0.76 | 0.94 | 0.002 |
| CRP (Δ 10 mg/L) | 131 | 0.69 | 0.50 | 0.96 | 0.026 |
| dsDNA (10 IU/mL) | 134 | 0.99 | 0.97 | 1.002 | 0.076 |

Stratifying the patient population based on prednisone treatment status revealed a stronger association between changes in disease activity and iC3b concentration or iC3b/total C3 ratio which was upheld in multivariate analyses below. As a result, iC3b concentration or iC3b/C3 ratio may be useful for monitoring treatment response in SLE patients who are receiving prednisone treatment for active disease.

In a multivariate analysis in patients who received prednisone treatment in this Example, Table 13 shows that when wb_iC3b and ESR were jointly included in the same cumulative logistic regression model, wb_iC3b was not significant; however, ESR was statistically significantly predictive of SLE flare activity. Table 14 shows that when wb_iC3b and CRP were jointly included in the same cumulative logistic regression model, wb_iC3b was significant; however, CRP was no longer statistically significantly predictive of SLE flare activity.

TABLE 13

Multiple cumulative logistic regression analysis with GEE for the flare outcome predicted by significant predictors in 44 patients during 129 visits

| Predictor Variable | N | OR | Lower 95% CI | Upper 95% CI | p-value for Beta (OR) |
|---|---|---|---|---|---|
| Wb_iC3b (Δ 1 μg/mL) | 129 | 0.89 | 0.78 | 1.02 | 0.104 |
| ESR (Δ 10 mm/hr) | 129 | 0.90 | 0.81 | 0.99 | 0.036 |

TABLE 14

Multiple cumulative logistic regression analysis with GEE for the flare outcome predicted by significant predictors in 44 patients during 129 visits

| Predictor Variable | N | OR | Lower 95% CI | Upper 95% CI | p-value for Beta (OR) |
|---|---|---|---|---|---|
| Wb_iC3b (Δ 1 μg/mL) | 129 | 0.86 | 0.76 | 0.97 | 0.017 |
| CRP (Δ 10 mg/L) | 129 | 0.73 | 0.52 | 1.02 | 0.036 |

Table 15 shows that multiple cumulative logistic regression analysis with GEE for the flare outcome jointly predicted by significant predictors in 44 patients who received prednisone treatment at any visit. Both iC3b/total C3 ratio and CRP were significant predictors for clinically meaningful change. For every 1 unit increase in the ratio, the odds of getting clinically meaningful improvement decreased by 7% or the odds of getting clinically meaningful worsening increased by 8% when CRP was held constant. Other predictor variables were not significant in the final model. When iC3b/C3 ratio and ESR were jointly included in the same cumulative logistic regression model, neither iC3b/C3 ratio nor ESR was statistically significantly predictive of SLE flare activity. The data are not shown.

TABLE 15

Multiple cumulative logistic regression analysis with GEE for the flare outcome predicted by significant predictors in 44 patients during 128 visits

| Predictor Variable | N | OR | Lower 95% CI | Upper 95% CI | p-value for Beta (OR) |
|---|---|---|---|---|---|
| iC3b/C3 ratio ($\Delta$ 1 unit) | 128 | 0.93 | 0.90 | 0.96 | <0.001 |
| CRP ($\Delta$ 10 mg/L) | 128 | 0.69 | 0.50 | 0.96 | 0.029 |

In sum, this Example shows that 1) iC3b concentration and iC3b/C3 ratio can distinguish SLE flare from non-flare 2) changes in iC3b concentration and changes in iC3b/C3 ratio between clinic visits are associated with changes in SLE disease activity and 3) in multivariate analyses, iC3b concentration and iC3c/C3 ratio were significantly associated with changes in disease activity when current standard of care laboratory values (e.g. dsDNA, C3, C4, ESR, CRP, etc.) were not. As a result, some embodiments provide methods and compositions for monitoring iC3b concentration and/or iC3b/C3 ratio values over time that enable earlier detection of SLE disease activity and flares, leading to earlier interventions and also monitoring of treatment response to enable discontinuation of toxic drugs sooner. Each outcome will improve disease management strategies and contribute to better outcomes in autoimmune diseases, for example, SLE.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A method for treating a pregnant human at risk of an adverse pregnancy outcome comprising:
   (i) detecting in a first sample of blood or urine from the pregnant human a first level of iC3b, intact C3, and/or total C3 at a first time point during the first, second, or third trimester of pregnancy;
   (ii) detecting in a second sample of blood or urine from the pregnant human a second level of iC3b, intact C3, and/or total C3 at a second time point during the third trimester of pregnancy;
   (iii) comparing the first and second levels;
   (iv) diagnosing the pregnant human as being at risk of an adverse pregnancy outcome by determining that the first and second levels are:
      (a) iC3b and the second level is higher than the first level; and/or
      (b) iC3b and intact C3 and the ratio of intact C3 to iC3b is the same as or lower than the first level; and/or
      (c) total C3 and the second level is the same as or lower than the first level; and
   (v) treating the pregnant human diagnosed as being at risk of an adverse pregnancy outcome with a treatment comprising administration of one or more of steroids, non-steroidal anti-inflammatory drugs (NSAIDs), hydroxychloroquine, chloroquine, quinacrine, methotrexate, azathioprine, cyclophosphamide, chlorambucil, cyclosporine, mycophenolate mofetil, rituximab, belimumab, complement inhibitors, plasmapheresis, delivery of the fetus, aspirin, one or more agents for treatment of hypertension, and/or one or more agents for treatment of eclamptic seizures.

2. The method of claim 1, wherein one or more antibodies is used to determine the first and/or second levels of iC3b, intact C3 and/or total C3 in the first or second samples.

3. The method of claim 2, wherein a lateral flow assay is used to determine the first and/or second levels of iC3b, intact C3 and/or total C3 in the first or second samples.

4. The method of claim 1, wherein the treatment is or comprises part of a combination therapy administered to the subject.

5. The method of claim 1, wherein the blood comprises whole blood, serum, plasma, or any combination thereof.

6. A method for treating a pregnant human at risk of an adverse pregnancy outcome comprising:
   (i) detecting in a sample of blood or urine from the pregnant human a level of iC3b, total C3, and/or iC3b and intact C3, during the first, second, or third trimester of pregnancy;
   (ii) comparing the level of total C3, iC3b, and/or iC3b and intact C3 from the pregnant human to one or more reference levels;
   (iii) diagnosing the pregnant human as being at risk of an adverse pregnancy outcome by determining that the level from the pregnant human is outside of a range of normal levels; and
   (iv) treating the pregnant human diagnosed as being at risk of an adverse pregnancy outcome with a treatment comprising-administration of one or more of steroids, non-steroidal anti-inflammatory drugs (NSAIDs), hydroxychloroquine, chloroquine, quinacrine, methotrexate, azathioprine, cyclophosphamide, chlorambucil, cyclosporine, mycophenolate mofetil, rituximab, belimumab, complement inhibitors, plasmapheresis, delivery of the fetus, aspirin, one or more agents for treatment of hypertension, and/or one or more agents for treatment of eclamptic seizures.

7. The method of claim 1 or claim 6, wherein the risk is determined between about one day and about three months before it occurs.

8. The method of claim 1 or claim 6, wherein, after administration of the one or more treatments, the adverse pregnancy outcome does not occur.

9. The method of claim 6, wherein one or more antibodies is used to determine the level of iC3b, intact C3 and/or total C3 in the sample.

10. The method of claim 6, wherein a lateral flow assay is used to determine the level of iC3b, intact C3 and/or total C3 in the sample.

11. The method of claim 6, wherein the blood comprises whole blood, serum, plasma, or any combination thereof.

12. The method of claim 6 wherein the treatment is or comprises part of a combination therapy administered to the subject.

* * * * *